United States Patent
Kondracki et al.

(10) Patent No.: US 11,976,250 B2
(45) Date of Patent: May 7, 2024

(54) SULFURIZED ADDITIVES WITH LOW LEVELS OF ALKYL PHENOLS

(71) Applicant: Afton Chemical Corporation, Richmond, VA (US)

(72) Inventors: Paul Kondracki, Richmond, VA (US); Edward Standefer, Chester, VA (US); Peter Hou, Chesterfield, VA (US)

(73) Assignee: Afton Chemical Corporation, Richmond, VA (US)

( * ) Notice: Subject to any disclaimer, the term of this patent is extended or adjusted under 35 U.S.C. 154(b) by 0 days.

(21) Appl. No.: 18/145,155

(22) Filed: Dec. 22, 2022

(65) Prior Publication Data

US 2023/0235241 A1   Jul. 27, 2023

Related U.S. Application Data

(62) Division of application No. 17/585,046, filed on Jan. 26, 2022, now Pat. No. 11,572,523.

(51) Int. Cl.
| | |
|---|---|
| *C10M 159/18* | (2006.01) |
| *C07C 39/235* | (2006.01) |
| *C07G 99/00* | (2009.01) |
| *C10M 133/08* | (2006.01) |
| *C10M 135/02* | (2006.01) |
| *C10N 10/02* | (2006.01) |
| *C10N 10/04* | (2006.01) |
| *C10N 30/00* | (2006.01) |
| *C10N 30/04* | (2006.01) |

(52) U.S. Cl.
CPC ......... *C10M 135/02* (2013.01); *C07C 39/235* (2013.01); *C07G 99/0024* (2022.08); *C10M 133/08* (2013.01); *C10M 159/18* (2013.01); *C10N 2010/02* (2013.01); *C10N 2010/04* (2013.01); *C10N 2030/04* (2013.01); *C10N 2030/52* (2020.05)

(58) Field of Classification Search
CPC ............. C10M 135/02; C10M 133/08; C10M 159/18; C10M 159/22; C10M 2215/062; C10M 2219/088; C10M 135/30; C10M 2219/089; C07C 39/235; C07G 99/0024; C07G 99/002; C10N 2010/02; C10N 2010/04; C10N 2030/04; C10N 2030/52
See application file for complete search history.

(56) References Cited

U.S. PATENT DOCUMENTS

| | | |
|---|---|---|
| 1,065,595 A | 6/1913 | Demary |
| 2,140,811 A | 12/1938 | Poole |
| 2,680,096 A | 6/1954 | Walker et al. |
| 3,178,663 A | 4/1965 | Kahn |
| 3,185,647 A | 5/1965 | Anderson et al. |
| 3,189,544 A | 6/1965 | Ratner et al. |
| 3,256,185 A | 6/1966 | Le Suer |
| 3,278,550 A | 10/1966 | Norman et al. |
| 3,312,619 A | 4/1967 | Vineyard |
| 3,366,569 A | 1/1968 | Norman et al. |
| 3,367,867 A | 2/1968 | Abbott et al. |
| 3,367,981 A | 2/1968 | Napolitano |
| 3,372,116 A | 3/1968 | Meinhardt |
| 3,390,086 A | 6/1968 | O'Halloran |
| 3,403,102 A | 9/1968 | Le Suer |
| 3,410,798 A | 11/1968 | Cohen |
| 3,458,530 A | 7/1969 | Siegel et al. |
| 3,470,098 A | 9/1969 | O'Halloran |
| 3,502,677 A | 3/1970 | Le Suer |
| 3,519,564 A | 7/1970 | Vogel |
| 3,546,243 A | 12/1970 | Coupland |
| 3,573,205 A | 3/1971 | Lowe et al. |
| 3,634,515 A | 1/1972 | Piasek et al. |
| 3,649,229 A | 3/1972 | Otto |
| 3,700,666 A | 10/1972 | Robin et al. |
| 3,708,522 A | 1/1973 | Le Suer |
| 3,749,695 A | 7/1973 | de Vries |
| 3,801,507 A | 4/1974 | Hendrickson et al. |
| 3,859,318 A | 1/1975 | Lesuer |
| 3,865,740 A | 2/1975 | Goldschmidt |
| 3,865,813 A | 2/1975 | Gergel |
| 3,954,639 A | 5/1976 | Liston |
| 4,021,419 A | 5/1977 | Karn |
| 4,081,386 A | 3/1978 | Sowerby |
| 4,152,499 A | 5/1979 | Boerzel et al. |
| 4,234,435 A | 11/1980 | Meinhardt et al. |
| 4,259,194 A | 3/1981 | DeVries et al. |
| 4,259,195 A | 3/1981 | King et al. |
| 4,261,843 A | 4/1981 | King et al. |
| 4,263,152 A | 4/1981 | King et al. |
| 4,265,773 A | 5/1981 | DeVries et al. |
| 4,272,387 A | 6/1981 | King et al. |
| 4,283,295 A | 8/1981 | DeVries et al. |
| 4,285,822 A | 8/1981 | deVries et al. |
| 4,379,064 A | 4/1983 | Cengel et al. |
| 4,482,464 A | 11/1984 | Karol et al. |
| 4,521,318 A | 6/1985 | Karol |
| 4,554,086 A | 11/1985 | Karol et al. |
| 4,579,675 A | 4/1986 | Sawicki et al. |
| 4,612,132 A | 9/1986 | Wollenberg et al. |
| 4,614,522 A | 9/1986 | Buckley |
| 4,614,603 A | 9/1986 | Wollenberg |
| 4,617,137 A | 10/1986 | Plavac |

(Continued)

FOREIGN PATENT DOCUMENTS

| | | | |
|---|---|---|---|
| EP | 0092415 B1 | 8/1985 | |
| EP | 1344812 A1 * | 9/2003 | ........... C07C 51/414 |

(Continued)

OTHER PUBLICATIONS

International Search Report and Written Opinion issued in Application No. PCT/US2023/060977 dated May 8, 2023, 14 pages.

*Primary Examiner* — Taiwo Oladapo
(74) *Attorney, Agent, or Firm* — Honigman LLP

(57) ABSTRACT

The present disclosure provides a detergent additives and methods for preparing a sulfurized alkyl phenate product to achieve a high sulfurization ratio and low levels of unsulfurized alkyl phenols.

20 Claims, No Drawings

(56) References Cited

U.S. PATENT DOCUMENTS

| | | |
|---|---|---|
| 4,617,138 A | 10/1986 | Wollenberg |
| 4,636,322 A | 1/1987 | Nalesnik |
| 4,645,515 A | 2/1987 | Wollenberg |
| 4,646,860 A | 3/1987 | Owens et al. |
| 4,647,390 A | 3/1987 | Buckley, III et al. |
| 4,648,886 A | 3/1987 | Buckley, III et al. |
| 4,648,980 A | 3/1987 | Erdman |
| 4,652,387 A | 3/1987 | Andress, Jr. et al. |
| 4,663,062 A | 5/1987 | Wollenberg |
| 4,663,064 A | 5/1987 | Nalesnik et al. |
| 4,666,459 A | 5/1987 | Wollenberg |
| 4,666,460 A | 5/1987 | Wollenberg |
| 4,668,246 A | 5/1987 | Wollenberg |
| 4,670,170 A | 6/1987 | Wollenberg |
| 4,699,724 A | 10/1987 | Nalesnik et al. |
| 4,710,308 A | 12/1987 | Stauffer |
| 4,713,189 A | 12/1987 | Nalesnik et al. |
| 4,713,191 A | 12/1987 | Nalesnik |
| 4,857,214 A | 8/1989 | Papay et al. |
| 4,948,386 A | 8/1990 | Sung et al. |
| 4,963,275 A | 10/1990 | Gutierrez et al. |
| 4,963,278 A | 10/1990 | Blain et al. |
| 4,971,598 A | 11/1990 | Andress et al. |
| 4,971,711 A | 11/1990 | Lundberg et al. |
| 4,973,411 A | 11/1990 | Jao et al. |
| 4,973,412 A | 11/1990 | Migdal et al. |
| 4,981,492 A | 1/1991 | Blain et al. |
| 5,026,495 A | 6/1991 | Emert et al. |
| 5,030,249 A | 7/1991 | Herbstman et al. |
| 5,039,307 A | 8/1991 | Herbstman et al. |
| 5,075,383 A | 12/1991 | Migdal et al. |
| 5,266,223 A | 11/1993 | Song et al. |
| 5,334,321 A | 8/1994 | Harrison et al. |
| 5,370,805 A | 12/1994 | Smrcka et al. |
| 5,650,381 A | 7/1997 | Gatto et al. |
| 5,739,355 A | 4/1998 | Gateau et al. |
| 6,107,257 A | 8/2000 | Valcho et al. |
| 6,281,320 B1 | 8/2001 | Kao et al. |
| RE37,363 E | 9/2001 | Gatto et al. |
| 6,300,291 B1 | 10/2001 | Hartley et al. |
| 6,723,685 B2 | 4/2004 | Hartley et al. |
| RE38,929 E | 1/2006 | Gatto et al. |
| 7,214,649 B2 | 5/2007 | Loper et al. |
| 7,253,231 B2 | 8/2007 | Devlin et al. |
| RE40,595 E | 12/2008 | Gatto et al. |
| 7,485,603 B2 | 2/2009 | Bera et al. |
| 7,645,726 B2 | 1/2010 | Loper |
| 7,732,390 B2 | 6/2010 | Kadkhodayan et al. |
| 7,786,057 B2 | 8/2010 | Bera et al. |
| 7,897,696 B2 | 3/2011 | Huang et al. |
| 8,048,831 B2 | 11/2011 | Loper |
| 8,425,629 B2 | 4/2013 | Jackson et al. |
| 8,513,172 B2 | 8/2013 | Baum et al. |
| 8,933,002 B2 | 1/2015 | Sinquin et al. |
| 9,453,089 B2 | 9/2016 | Shaikh et al. |
| 9,988,590 B1 | 6/2018 | Kwak |
| 10,144,900 B1 | 12/2018 | Kwak |
| 2008/0040968 A1* | 2/2008 | Malfer ............. C10M 159/16 508/542 |
| 2008/0182468 A1 | 7/2008 | Dharmarajan et al. |
| 2009/0258803 A1 | 10/2009 | Harrison |
| 2009/0298964 A1 | 12/2009 | Jacob et al. |
| 2010/0139944 A1 | 6/2010 | Guo et al. |
| 2010/0261808 A1 | 10/2010 | Schadler et al. |
| 2012/0101017 A1 | 4/2012 | Duggal |
| 2013/0165359 A1 | 6/2013 | Gibbs et al. |
| 2014/0061533 A1 | 3/2014 | Schultz Hume et al. |
| 2014/0275501 A1 | 9/2014 | Capanema et al. |
| 2017/0096502 A1 | 4/2017 | Storey et al. |
| 2017/0211008 A1 | 7/2017 | Walker et al. |
| 2017/0335148 A1 | 11/2017 | Chou |
| 2020/0318025 A1 | 10/2020 | Sampler et al. |
| 2020/0377815 A1 | 12/2020 | Sampler et al. |
| 2020/0377817 A1 | 12/2020 | Sampler et al. |

FOREIGN PATENT DOCUMENTS

| | | |
|---|---|---|
| EP | 1602707 A1 | 12/2005 |
| GB | 785468 A | 10/1957 |
| GB | 2440811 A | 2/2008 |
| WO | 9406897 A1 | 3/1994 |
| WO | 2005026299 A2 | 3/2005 |
| WO | 2021035087 A1 | 2/2021 |
| WO | 2021161199 A1 | 8/2021 |

* cited by examiner

SULFURIZED ADDITIVES WITH LOW LEVELS OF ALKYL PHENOLS

CROSS REFERENCE TO RELATED APPLICATION

This Application is a Division of U.S. patent application Ser. No. 17/585,046 filed on Jan. 26, 2022, the entire contents of which is incorporated herein by reference in its entirety.

TECHNICAL FIELD

The present disclosure generally relates to lubricating oil compositions and sulfurized additives therefor with low levels of unsulfurized alkyl phenols.

BACKGROUND

Metal salts of sulfurized alkyl phenols, otherwise known as alkyl phenates, tend to be useful lubricating oil additives. These additives may function, for example, as detergents, friction modifiers, and/or dispersants while providing an alkalinity base to aid in the neutralization of acids generated during automotive operation, when used in a lubricant in an automotive application. Unsulfurized variants of the alkyl phenates or phenols have reduced utility and tend to be less desired in the lubricant for many reasons. As such, additive manufacturers seek to minimize levels of unsulfurized alkyl phenates and/or alkyl phenols in their additives. Current methods, however, have one or more shortcomings when seeking to minimize levels of unsulfurized alkyl phenate/phenol variants when the additives are also overbased.

SUMMARY AND TERMS

In accordance with one embodiment, a sulfurized metal phenate detergent comprising a compound of Formula I and a compound of Formula II is described herein. In approaches, the compounds of Formula I and II have structures including the following:

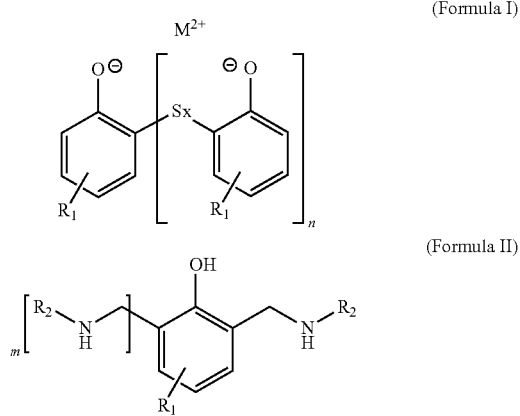

wherein each $R_1$, independently, is one of an alkyl group, an aryl group, an alkylaryl group, or arylalkyl group; $R_2$ is one of hydrogen, an alkyl group, an alkylamino group, or a hydroxyalkyl group; x is an integer from 1 to 4; n is an integer from 1 to 3; m is an integer of 0 or 1; and $M^{2+}$ is a divalent metal ion.

In other embodiments or approaches, the sulfurized metal phenate detergent described in the previous paragraph includes optional features or embodiments. These optional features or embodiments may include, in any combination: wherein $R_1$ is a C8 to C20 alkyl group; and/or wherein $R_2$ is methyl; and/or wherein $R_2$ has a structure of $-R_4N(R_5)(R_5)$ wherein $R_4$ is a C1 to C10 hydrocarbyl group and each $R_5$ is, independently, a C1 to C4 alkyl group; and/or wherein the detergent includes about 0.01 to about 0.5 weight percent of the compound of Formula II; and/or further comprising about 0.5 weight percent or less of an unsulfurized alkyl phenol; and/or wherein the detergent has a TBN of 0 to 300 mg KOH as measured by the method of ASTM D-2896; and/or wherein each of the compound of Formula I, the compound of Formula II, or both has less than about 15 weight percent of $R_1$ substitution at the ortho position; and/or wherein the detergent includes up to about 100,000 ppm of the metal provided by an alkali or alkaline metal and up to about 65,000 ppm of sulfur; and/or wherein the alkali or alkaline metal is one of lithium, potassium, sodium, magnesium, calcium, barium, aluminum, or combinations thereof.

In another embodiment, a lubricating oil composition comprising the metal phenate detergent of any embodiment of the previous two paragraphs and one or more base oils of lubricating viscosity.

In yet another embodiment, a process is described for preparing a sulfurized alkyl phenate product. In approaches, the process comprises, in any order, sulfurizing an alkyl phenol with a source of sulfur to provide a sulfurized alkyl phenol, wherein the alkyl phenol is derived from an alkylation of a phenol, neutralizing and optionally overbasing the sulfurized alkyl phenol in the presence of a solvent to provide a sulfurized alkyl phenate composition including a mixture of a sulfurized alkyl phenate and a residual unsulfurized alkyl phenol, wherein the sulfurizing, the neutralizing, and the optional overbasing may occur in any order; and post processing the sulfurized alkyl phenate composition to obtain the sulfurized alkyl phenate product, wherein the post processing includes reacting the sulfurized alkyl phenate composition with a triazine compound.

In yet other embodiments or approaches, the process of the previous paragraph may include optional features or embodiments. These optional features may include one or more of the following embodiments, in any combination: wherein the source of sulfur includes elemental sulfur, sulfur monochloride, sulfur dichloride, hydrogen sulfide, sulfur dioxide, sulfide hydrates, or combinations thereof; and/or wherein a mol ratio of the sulfur source to the alkyl phenol is about 0.1 to about 3.5; and/or wherein the neutralizing and/or the optional overbasing includes contacting the sulfurized alkyl phenol with an alkali or alkaline earth metal salt; and/or wherein the alkali or alkaline earth metal salt is lithium hydroxide, potassium hydroxide, sodium hydroxide, magnesium hydroxide, calcium hydroxide, barium hydroxide, aluminum hydroxide, lithium oxide, magnesium oxide, calcium oxide, barium oxide, or combinations thereof; and/or wherein the triazine compound has the structure of Formula III

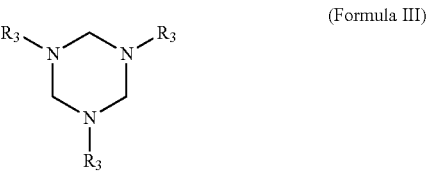

wherein each $R_3$ is, independently, hydrogen, a hydrocarbyl group, an alkyl group, an amino group, a polyamino group, an alkylamino group, a dialklyaminoalkyl group, a C1 to C10 hydrocarbyl group or a —$R_4N(R_5)(R_5)$ group where each of $R_4$ and $R_5$ is, independently, a C1 to C10 hydrocarbyl group; and/or further comprising about 0.5 weight percent or less of an unsulfurized alkyl phenol; and/or wherein the sulfurized alkyl phenate product includes a compound of Formula I and a compound of Formula II:

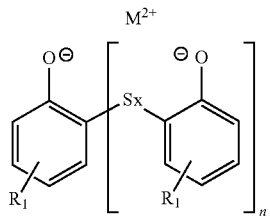
(Formula I)

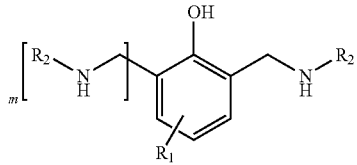
(Formula II)

wherein each $R_1$, independently, is an alkyl group, an aryl group, an alkylaryl group, or arylalkyl group; $R_2$ is an alkyl group, an aminoalkyl group, or a hydroxyalkyl group; x is an integer from 1 to 4; n is an integer from 1 to 3; m is an integer of 0 or 1; and $M^{2+}$ is a divalent metal ion; and/or wherein $R_1$ is a C8 to C20 alkyl group; and/or wherein $R_2$ is methyl or has the structure —$R_4N(R_5)(R_5)$ wherein $R_4$ is a C1 to C10 hydrocarbyl group and each $R_5$ is, independently, a C1 to C4 alkyl group.

In yet other embodiments, a sulfurized metal phenate detergent prepared by the process of any embodiment of the previous two paragraphs is described herein.

In yet further embodiments, use of a sulfurized metal phenate composition as a detergent is described herein where the sulfurized metal phenate composition is any embodiment as described in this summary.

The following definitions of terms are provided in order to clarify the meanings of certain terms as used herein.

The terms "oil composition," "lubrication composition," "lubricating oil composition," "lubricating oil," "lubricant composition," "lubricating composition," "fully formulated lubricant composition," and "lubricant" are considered synonymous, fully interchangeable terminology referring to the finished lubrication product comprising a major amount of a base oil plus a minor amount of an additive composition.

As used herein, the terms "additive package," "additive concentrate," and "additive composition" are considered synonymous, fully interchangeable terminology referring the portion of the lubricating oil composition excluding the major amount of base oil stock mixture.

Unless otherwise specified, the term "overbased" relates to metal salts, such as metal salts of sulfonates, carboxylates, salicylates, and/or phenates, wherein the amount of metal present exceeds the stoichiometric amount. Such salts may have a conversion level in excess of 100% (i.e., they may comprise more than 100% of the theoretical amount of metal needed to convert the acid to its "normal," "neutral" salt). The expression "metal ratio," often abbreviated as MR, is used to designate the ratio of total chemical equivalents of metal in the overbased salt to chemical equivalents of the metal in a neutral salt according to known chemical reactivity and stoichiometry. In a normal or neutral salt, the metal ratio is one and in an overbased salt, MR, is greater than one. They are commonly referred to as overbased, hyperbased, or superbased salts and may be salts of organic sulfur acids, carboxylic acids, salicylates, sulfonates, and/or phenols.

The term "alkaline earth metal" relates to calcium, barium, magnesium, and strontium, and the term "alkali metal" refers to lithium, sodium, potassium, rubidium, and cesium.

As used herein, unless specified otherwise, the term "hydrocarbyl" or "hydrocarbyl substituent" or "hydrocarbyl group" is used in its ordinary sense, which is well-known to those skilled in the art. Specifically, it refers to a group having a carbon atom directly attached to the remainder of the molecule and having a predominantly hydrocarbon character. Each hydrocarbyl group is independently selected from hydrocarbon substituents, and substituted hydrocarbon substituents containing one or more of halo groups, hydroxyl groups, alkoxy groups, mercapto groups, nitro groups, nitroso groups, amino groups, pyridyl groups, furyl groups, imidazolyl groups, oxygen, and nitrogen, and wherein no more than two non-hydrocarbon substituents are present for every ten carbon atoms in the hydrocarbyl group.

As used herein, unless specified otherwise, the term "hydrocarbylene substituent" or "hydrocarbylene group" is used in its ordinary sense, which is well-known to those skilled in the art. Specifically, it refers to a group that is directly attached at two locations of the molecule to the remainder of the molecule by a carbon atom and having predominantly hydrocarbon character. Each hydrocarbylene group is independently selected from divalent hydrocarbon substituents, and substituted divalent hydrocarbon substituents containing halo groups, alkyl groups, aryl groups, alkylaryl groups, arylalkyl groups, hydroxyl groups, alkoxy groups, mercapto groups, nitro groups, nitroso groups, amino groups, pyridyl groups, furyl groups, imidazolyl groups, oxygen and nitrogen, and wherein no more than two non-hydrocarbon substituents is present for every ten carbon atoms in the hydrocarbylene group.

As used herein, the term "percent by weight", unless expressly stated otherwise, means the percentage the recited component represents to the weight of the entire composition.

The terms "soluble," "oil-soluble," or "dispersible" used herein may, but does not necessarily, indicate that the compounds or additives are soluble, dissolvable, miscible, or capable of being suspended in the oil in all proportions. The foregoing terms do mean, however, that they are, for instance, soluble, suspendable, dissolvable, or stably dispersible in oil to an extent sufficient to exert their intended effect in the environment in which the oil is employed. Moreover, the additional incorporation of other additives may also permit incorporation of higher levels of a particular additive, if desired.

The term "TBN" as employed herein is used to denote the Total Base Number in mg KOH/g as measured by the method of ASTM D2896.

The term "lime" as employed herein refers to, for example, calcium hydroxide, calcium oxide, and the like compounds, also known as slaked lime or hydrated lime.

The term "alkyl" as employed herein, unless specified otherwise, refers to straight, branched, cyclic, and/or substituted saturated chain moieties of from about 1 to about 100 carbon atoms. The term "alkenyl" as employed herein, unless specified otherwise, refers to straight, branched, cyclic, and/or substituted unsaturated chain moieties of from about 3 to about 10 carbon atoms. The term "aryl" as employed herein, unless otherwise specified, refers to single and multi-ring aromatic compounds that may include alkyl, alkenyl, alkylaryl, amino, hydroxyl, alkoxy, halo substituents, and/or heteroatoms including, but not limited to, nitrogen, oxygen, and sulfur.

The molecular weight for any embodiment herein may be determined with a gel permeation chromatography (GPC) instrument obtained from Waters or the like instrument and the data processed with Waters Empower Software or the like software. The GPC instrument may be equipped with a Waters Separations Module and Waters Refractive Index detector (or the like optional equipment). The GPC operating conditions may include a guard column, 4 Agilent PLgel columns (length of 300×7.5 mm; particle size of 5μ, and pore size ranging from 100-10000 Å) with the column temperature at about 40° C. Un-stabilized HPLC grade tetrahydrofuran (THF) may be used as solvent, at a flow rate of 1.0 mL/min. The GPC instrument may be calibrated with commercially available polystyrene (PS) standards having a narrow molecular weight distribution ranging from 500-380,000 g/mol. The calibration curve can be extrapolated for samples having a mass less than 500 g/mol. Samples and PS standards can be in dissolved in THF and prepared at concentration of 0.1 to 0.5 wt. % and used without filtration. GPC measurements are also described in U.S. Pat. No. 5,266,223, which is incorporated herein by reference. The GPC method additionally provides molecular weight distribution information; see, for example, W. W. Yau, J. J. Kirkland and D. D. Bly, "Modern Size Exclusion Liquid Chromatography", John Wiley and Sons, New York, 1979, also incorporated herein by reference.

Additional details and advantages of the disclosure will be set forth in part in the description that follows, and/or may be learned by practice of the disclosure. The details and advantages of the disclosure may be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

The present disclosure provides a detergent additive in the form of a composition or mixture including at least a sulfurized alkyl phenate with low levels of residual or unsulfurized alkyl phenols, lubricating oil compositions including such detergent additive, and methods for preparing the detergent additive in the context of a neutral to an overbased additive, such as a detergent with a TBN of at least about 0, at least about 20, at least about 50, at least about 100 and otherwise about 100 to about 500 as further discussed below.

In one approach or embodiment, the present disclosure generally relates to a detergent additive or detergent composition including at least a sulfurized metal phenate detergent including a compound of Formula Ia, optionally a compound of Formula Ib, and a compound of Formula II:

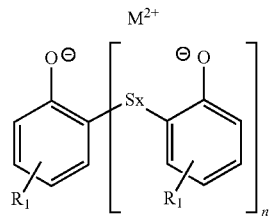

Formula Ia

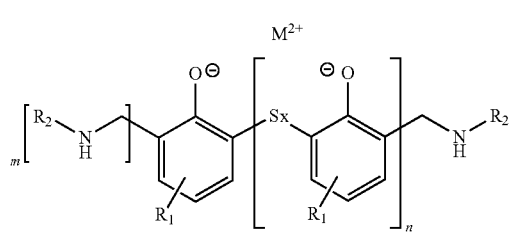

Formula Ib

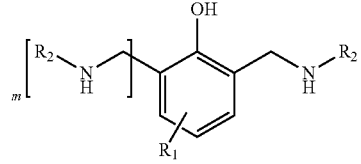

Formula II wherein each $R_1$, independently, is an alkyl group, an aryl group, an alkylaryl group, or arylalkyl group (preferably, $R_1$ is a C8 to C20 alkyl or hydrocarbyl group and most preferably, a C12 linear or branched alkyl or hydrocarbyl group); $R_2$ is one of hydrogen, an alkyl group, an alkylamino group, or a hydroxyalkyl group; x is an integer from 1 to 4; n is an integer from 1 to 3; each m is, independently, an integer of 0 or 1; and $M^{2+}$ is a divalent metal ion. Preferably, the $R_1$ groups are predominately located in the para-position on the aromatic ring as discussed more below. Mannich reactions forming the post-reactant amine (discussed more below) generating the compounds of Formula Ia, Formula Ib, and/or Formula II may be through any open ortho-, meta-, or para-positions on the aromatic ring, but amine reacting is preferably located at the ortho-position as shown in the structures above. As also shown above, sulfur bridging in Formula Ia or Ib is predominately at the ortho-position, but may be other positions on the aromatic ring depending on the application and/or reaction conditions. Mannich reactions forming the post-reactant amine may also generate di-additions to the aromatic ring (e.g., ortho and para, ortho and meta, or meta and para) depending on the application.

Overbased sulfurized alkyl phenates are made by sulfurization, neutralization, and/or carbonation. These reactions can be carried out in any order, at the same time, or in a specific sequence depending on the application. Sulfurization and neutralization, for instance and within any order of sequence or at the same time, is usually completed prior to carbonation. In general, the detergent additives or compositions herein are obtained from first neutralizing alkyl phenols, then the neutralized alkyl phenols are sulfurized with a source of sulfur to provide a sulfurized and neutralized alkyl phenol. The sulfurized and neutralized alkyl phenol is then optionally overbased in the presence of a solvent to provide a neutral to an optionally overbased and sulfurized alkyl phenate additive or composition. Post processing of this additive/composition is then conducted in the presence of a triazine compound in amounts effective to reduce the levels of unsulfurized or residual alkyl phenol/phenate variants to low or ultra-low levels of about 0.5 weight percent or less (in some approaches, about 0.2 weight percent or less, and in other approaches, about 0.1 weight percent or less). The triazine compound reacts with the phenate and/or unsulfurized alkyl phenol via a Mannich reaction and, alternatively, may also be through an in-situ generation via an amine and formaldehyde or paraformaldehyde post reactants. More specifics of the additives and methods of producing such additives are discussed below.

Alkylation of Phenols

The sulfurized alkyl phenate of the detergent compositions herein is first obtained through alkylation of a suitable phenol (or hydroxyaromatic) compound with one or more olefins and/or oligomers derived from olefins. Suitable phenol or hydroxyaromatic compounds include monohydroxy and/or polyhydroxy aromatic hydrocarbons having 1 to 4, and in some approaches, 1 to 3, hydroxyl groups. Suitable compounds include but are not limited to phenol, catechol, resorcinol, hydroquinone, pyrogallol, cresol, and the like and mixtures thereof. Preferred starting compounds include phenol.

The alkylating agent includes one or more olefins and/or oligomers derived from olefins selected from ethylene, propylene, butylene, isobutylene, or mixtures thereof. Suitable olefins include isobutylenes, propylene trimers and/or tetramers, butylene trimers and/or tetramers to suggest but a few examples, but other olefins may be present in the oligomer or alkyl group such as linear olefins, cyclic olefins, branched olefins other than propylene oligomers such as butylene or isobutylene oligomers, arylalkylenes and the like and mixtures thereof. The alkylation may be conducted in the presence of a catalyst such as Lewis acid catalysts, solid acid catalysts, trifluoromethanesulfonic acid, and other acidic molecular sieve catalysts. Exemplary Lewis acid catalysts are known to those of skill and may include aluminum trichloride, aluminum tribromide, aluminum triiodide, boron trifluoride, boron tribromide, boron triiodide and the like. In some approaches, a molar ratio of the phenol or hydroxyaromatic compound to the one or more olefins or oligomers may be about 10:1 to about 0.5:1, and in other approaches, about 5:1 to about 2:1. The oligomer alkyl group is commonly attached to the phenol or hydroxyaromatic compound in the ortho and/or para positions and, preferably at the para-position, but other substitution may also be present depending on the application. For instance, the oligomer alkyl group (that is, the $R_1$ substituent in the formulas herein), may be about 85 to about 100 percent in the para-position on the aromatic ring and about 0 to about 15 percent in the ortho-position of the aromatic ring and, in some approaches, about 0 to about 5 percent di-substituted.

Neutralization

Neutralization is done by the alkyl phenols reacting with a metal base. In one approach, neutralization is performed by contacting the alkyl phenol with a metal base under reactive conditions, in some approaches, in a liquid hydrocarbon diluent with a promotor to provide a phenate or salt of the alkylhydroxyaromatic compound. In some instances, the reaction can be conducted under an inert gas, such as nitrogen. The metal base may be added either in a single addition or in multiple additions at various times during the reaction if needed for certain applications. Neutralization may occur via the exemplary reaction Scheme I shown below, but other reactions may proceed as needed depending on the selected order of the sulfurization, neutralization, and/or overbasing as well as the various application, materials, and conditions:

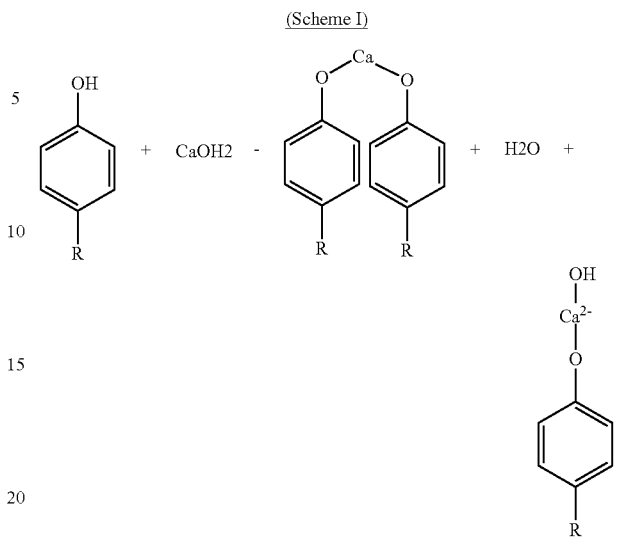

Exemplary metal base reactants include hydroxides, oxides, or alkoxides of a metal such as but not limited to an alkali metal salt derived from a metal base selected from an alkali hydroxide, alkali oxide or an alkali alkoxide, or an alkaline earth metal salt derived from a metal base selected from an alkaline earth hydroxide, alkaline earth oxide or alkaline earth alkoxide. Suitable metal base compounds include lithium hydroxide, potassium hydroxide, sodium hydroxide, magnesium hydroxide, calcium hydroxide, barium hydroxide, ammonium hydroxide, and/or aluminum hydroxide. Other examples of metal basic compounds include lithium oxide, magnesium oxide, calcium oxide and barium oxide. In a preferred example, the alkaline earth metal base is lime or calcium hydroxide. Additives may be borated as needed depending on the application and use.

In optional approaches, the neutralization solvent is a higher boiling point, such as solvents having a boiling point of about 100° C. or higher at the noted pressures such as ethylene glycol propylene glycol, and/or decanol and the like solvents. In such optional approaches and as used, herein, devoid or free of such compounds means the solvent has less than about 15 weight percent, less than about 5 weight percent, less than about 2 weight percent.

The neutralization reaction between the metal base and the alkyl phenol is conducted at conditions effective to maintain at elevated temperature. In one approach, neutralization occurs at temperatures of at least 100° C., in some approaches, at least about 120° C., in other approaches, at least about 150° C., and in yet preferred approaches, at temperatures no greater than about 180° C. The neutralization reaction may occur for about 1 hour to about 5 hours.

Sulfurization

The neutralized alkyl phenol or alkylhydroxyaromatic compound may be sulfurized by contacting with a sulfur source in a manner effective to achieve a high degree of sulfurization. In approaches, the sulfurization generally introduces sulfur-bridging groups between alkyl phenol or alkylhydroxyaromatic moieties. In some approaches, the sulfur bridging is $-S_y-$ or $-S_x-$ groups (shown in the exemplary structures below), wherein y or x is, independently, an integer from 1 to 4 and in other approaches, 1 to 3 and, in some approaches, 1 to 2 and/or with a total sulfur level provided by the additive of up to about 5 percent. The sulfur source may be any suitable sulfur, for example, elemental sulfur or a halide thereof such as sulfur monochloride or sulfur dichloride, hydrogen sulfide, sulfur dioxide and sodium sulfide hydrates. The sulfur can be employed either as molten sulfur or as a solid (powder or particulate) or as a solid suspension in a hydrocarbon liquid. An exemplary reaction scheme of sulfurization is shown below in reaction scheme II, but other reactions may proceed as needed depending on the application, materials, and conditions (Scheme II)

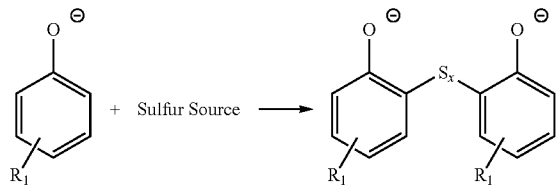

Sulfurization may occur, for example, at temperature of about 200° C. to about 250° C., in other approaches, about 225° C. to about 245° C. for a time effective to achieve the desired level of sulfurization, which may be about 1 to about 8 hours, about 2 to about 7 hours, or about 4 to about 7 hours.

Overbasing

Next, overbasing is optional, but preferred in some embodiments, and conducted either during or, alternatively, after the above-described neutralization and/or sulfurization. In one approach, the sulfurized alkyl phenol/alkyl phenate is overbased by reacting with an excess of the metal base and/or reacting with an acidic overbasing compound such as, for example, carbon dioxide or boric acid. In one approach, overbasing is via carbonation (a reaction with carbon dioxide) in the presence of solvent, such as any of the solvents from the solvent system described above with the neutralization. One convenient carbonation reaction is passing gaseous carbon dioxide through the reaction mixture. Excess solvents and any water formed during the overbasing reaction can be removed as needed by distillation either during or after the reaction as discussed further below.

In one embodiment, an exemplary overbasing reaction may be reacting the sulfurized alkyl phenol or salt thereof with an alkali or alkaline earth metal such as lime in the presence of carbon dioxide and the solvent system as already discussed above. Conveniently, the reaction may be conducted by bubbling gaseous carbon dioxide through the reaction and solvent system mixture. In one approach, overbasing occurs at temperatures of at least about 50° C., in some approaches, at least about 100° C., in other approaches, at least about 165° C., and in yet preferred approaches, at temperatures no greater than about 185° C. The degree of overbasing may be controlled by the quantity of the alkali or alkaline earth metal, amount of carbon dioxide and other reactants (if any) added to the reaction mixture as well as the reaction conditions used during the carbonation process. In approaches, overbasing or overbasing via carbonation occurs for a time sufficient to achieve a desired degree of overbasing or TBN and, in some approaches, may be about 30 minutes to about 180 minutes at the noted temperatures.

After the optional overbasing, the overbased and sulfurized alkyl phenate, such as the detergent compositions herein may have a TBN of at least about 0, at least about 20, at least about 50, at least about 100, or in other approaches, about 100 to about 500, about 100 to about 400, or about 150 to about 400, and in yet other approaches, about 200 to about 300, and in further approaches, about 220 to about 275. Preferably, the TBN of compositions herein may be about 100 to about 300 mg KOH as measured by ASTM D-2896. The resultant product may also have a level of residual or unsulfurized alkyl phenol after the optional overbasing, neutralizing, and sulfurization of about 1.0 weight percent or higher, in other approaches, about 1.5 weight percent or higher, and in yet other approaches, about 0.5 weight percent or higher. As discussed further below, the post processing herein is effective to reduce such levels of residual or unsulfurized alkyl phenol content in the detergents herein.

Post Processing

After the optional overbasing, the composition is often subjected to a number of steps to prepare a final sulfurized alkyl phenate product. Examples of post processing may include one or more of vacuum stripping, distillation, sparging, filtering, degassing, evaporation, wiped-film evaporating, centrifuging, diluting, liquid-liquid extraction, membrane separation, chromatography, absorption, supercritical extractions, and/or combinations thereof.

As noted above, the additives and compositions after the sulfurization, neutralization, and optional overbasing may include undesirably high amounts of unsulfurized or residual alkyl phenols or phenates. One preferred post-processing step herein is further reacting or post treating the sulfurized alkyl phenate composition, in any embodiment discussed previously and after the sulfurization, neutralization and the optional overbasing, with a triazine post-treatment reactant to minimize and further reduce any of the residual or unsulfured alkyl phenol/phenate within the composition.

In approaches, suitable triazine reactants for the post processing may include any triazine or substituted triazine (or mixtures thereof) that can react with a phenol compound and, in particular, triazines of Formula III below that can react with a phenol compound:

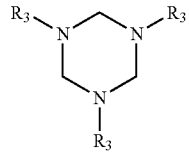

(Formula III)

wherein each $R_3$ is, independently, hydrogen, a hydrocarbyl group, an alkyl group, an amino group, a polyamino group, an alkylamino group, a dialklyaminoalkyl group, a hydroxyalkyl group and may be a C1 to C20 hydrocarbyl group (optionally, a C1 to C10 or C1 to C4 group) or a —$R_4$N($R_5$)($R_5$) group where each of $R_4$ and $R_5$ is, independently, a C1 to C10 hydrocarbyl group (preferably, $R_4$ is a C1 to C3 group and each $R_5$ is a C1 to C3 group, and more preferably, a methyl group). While the triazine of Formula III may be added as the post-reactant, the triazine may optionally be formed in-situ or the reaction product above may be formed in-situ from an amine and formaldehyde or paraformaldehyde added as post reactants. Alternatively, trioxane may be used as a formaldehyde equivalent.

Without wishing to be limited by theory, it is believed that the triazine reacts with the unsulfurized alkyl phenol (or sulfurized phenate) in the composition to form an alkyl phenol derivative having, for example, amino, polyamino, and/or alkylamino substitution. For instance, a simplified reaction scheme III below shows exemplary post processing believed to occur with the additives herein where the triazine compound of Formula III reacts with unsulfurized/residual alkyl phenol of the sulfurized phenate detergent/composition to form the alkyl phenol derivative of Formula II:

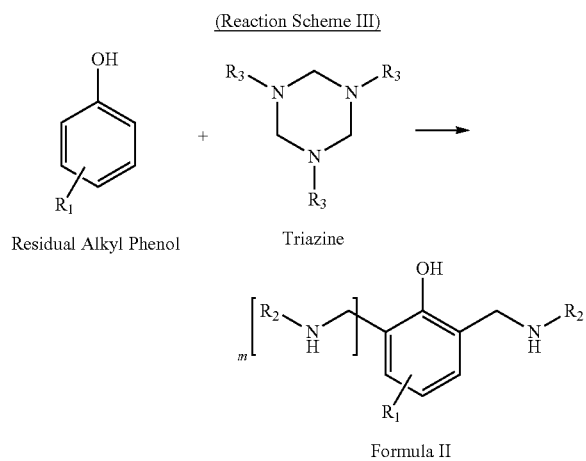

(Reaction Scheme III)

Residual Alkyl Phenol      Triazine

Formula II wherein each $R_1$, independently, is an alkyl group, an aryl group, an alkylaryl group, or arylalkyl group (preferably, a C8 to C20 linear or branched hydrocarbyl or alkyl group, or a C12 linear or branched alkyl or hydrocarbyl group); $R_2$ is hydrogen, an alkyl group (preferably a C1 to C4 group and most preferably a C1 group), an alkylamino group, a dialkylaminoalkyl group, or —$R_4N(R_5)(R_5)$ wherein $R_4$ is a C1 to C10 alkyl or hydrocarbyl group and each $R_5$ is, independently, a C1 to C4 alkyl group; $R_3$ is as discussed above, and m is an integer of 0 or 1. In some approaches, suitable triazines include trimethyl triazine, (tris)dimethylaminopropyl triazine, (tris)monoethyl triazine, or mixtures thereof. In general, suitable triazines may be obtained from any primary amine and formaldehyde or formaldehyde equivalents (e.g., trioxane and the like). The triazine post reactant may also react with the phenate in a similar reaction scheme to form residual amounts of the compound of Formula Ib above.

In approaches, the post processing with the triazine may include adding up to about 10 weight percent of the triazine, or about 0.5 to about 10 weight percent of the triazine (in other approaches, about 1 to about 8 weight percent, or about 2 about 6 weight percent of the desired triazine) to the sulfurized, neutralized, and optionally overbased phenate composition and reacting at temperatures of about 100° C. to about 230° C. (in other approaches, about 130° C. to about 150° C.). for about 1 to about 5 hours or for a time effective to achieve the desired level of unsulfurized phenol/phenate. In yet other approaches, the post reacting may be at a weight ratio of phenate reaction mass to the triazine of about 10:1 to about 20:1 and, in other approaches, about 15:1 to about 18:1. However, the amount of triazine may vary depending on the residual unsulfurized phenol content of the reaction mixture. Excess triazine may be removed, if needed, by heating to about 230° C. or higher under vacuum and/or through other suitable procedures.

In approaches and after the post processing, the compositions herein may include about 75 weight percent or more of the compound of Formula I discussed above (such about 80 weight percent or more, about 90 weight percent or more and, in some approaches, about 80 to about 95 weight percent) and about 5 weight percent or less of the compound of Formula II (such as about 0.01 to about 5 weight percent, about 0.1 to about 4 weight percent, or about 0.5 to about 3 weight percent); however, such amounts may vary depending on the circumstances, reactants, and starting materials. The methods, detergent compositions, and lubricating oil compositions with such detergents herein have low to ultra-low levels of the unsulfurized or residual alkyl phenol/phenate. In approaches, the detergent compositions and methods herein have less than about 0.5 weight percent, less than about 0.2 weight percent, less than about 0.1 weight percent, less than about 0.08 weight percent, or less than about 0.05 weight percent of the unsulfurized alkyl phenates/alkyl phenols or about 0.01 to about 0.5 weight percent or any range therein of the unsulfurized alkyl phenate/alkyl phenols. For instance, the post processing is effective such that the detergent compositions herein include amounts of unsulfurized alkyl phenate/alkyl phenol ranging from at least about 0.01 weight percent, at least about 0.02 weight percent, at least about 0.04 weight percent, at least about 0.05 weight percent, or at least about 0.08 weight percent to no more than about 0.5 weight percent, no more than about 0.2 weight percent, no more than about 0.16 weight percent, no more than about 0.12 weight percent, no more than about 0.1 weight percent, no more than about 0.08 weight percent, or even no more than about 0.05 weight percent of the unsulfurized alkyl phenol or phenate. At the same time, the detergent compositions herein include about 75 to about 95 weight percent of the sulfurized alkyl phenate of Formula I and about 0.01 to about 5 weight percent of the compound of Formula II (or other ranges within such endpoints); however, the amounts of the various compounds may vary depending on the applications and/or circumstances.

Unique to the detergent compositions and methods herein is that unsulfurized alkyl phenate or alkyl phenols generally do not need to be removed (such as after sulfurization or after any intermediate step) because the method steps herein consume and/or minimize any unsulfurized alkyl phenol, do not regenerate unsulfurized alkyl phenate or alkyl phenols within any of the various process steps, and/or rather, post treat any remaining unsulfurized alkyl phenol with triazine to tie-up or bond any remaining alkyl phenol with the various reaction products of the phenate processes herein. As such, the methods herein, therefore, avoid the expense and complexity of prior methods that necessitated the removal of residual and/or unsulfurized alkyl phenate/phenols either intermediate to the process or during post-processing steps. Additionally, the detergent compositions herein of a sulfurized alkyl phenate and one or more of the compounds of Formula I, Formula II, and/or residual amounts of Formula III may also include up to about 100,000 ppm of metal provided by an alkali or alkaline metal and up to about 65,000 ppm of sulfur and low levels of unsulfurized alkyl phenol/phenate of about 0.5 weight percent or below as discussed above.

Lubricating Oil Compositions

The optionally overbased and sulfurized alkyl phenate products described herein may be combined with a major amount of a base oil or base oil blend of lubricating viscosity (as described below) in combination with one or more further optional additives to produce a lubricating oil composition. In approaches, the lubricating oil compositions includes about 50 weight percent or more of the base oil, about 60 weight percent or more, about 70 weight percent or more, or about 80 weight percent or more to about 95 weight percent or less, about 90 weight percent or less, about 85 weight percent or less of the base oil as further discussed below.

In approaches, the lubricating oil compositions herein may include about 0.02 to about 5 weight percent of the optionally overbased and sulfurized alkyl phenate product, in other approaches, about 0.2 to about 3 weight percent, and in yet other approaches, about 0.2 to about 2 weight percent in a base oil or base oil blend.

In some approaches, the additives herein can be used as detergents in lubricating oils to neutralize acids and/or to help control rust, corrosion, and deposits. In addition, the detergents described herein may also be used in fuels, including but not limited to, gasoline, diesel, biodiesel, for spark, compression, and hybrid engines.

Lubricants, combinations of components, dispersant inhibitor packages, and/or individual components of the present description may be suitable for use in various types of lubricants such as automotive lubricants and/or greases, internal combustion engine oils, hybrid engine oils, hybrid engine oils, electric engine lubricants, drivetrain lubricants, transmission lubricants, gear oils, hydraulic lubricants, tractor hydraulic fluids, metalworking fluids, turbine engine lubricants, stationary engine lubricants, tractor lubricants, motorcycle lubricants, power steering fluids, clutch fluids, axle fluids, wet break fluids, and the like.

Suitable engine types may include, but are not limited to heavy-duty diesel, passenger car, light duty diesel, medium speed diesel, or marine engines. An internal combustion engine may be a diesel fueled engine, a gasoline fueled engine, a natural gas fueled engine, a bio-fueled engine, a mixed diesel/biofuel fueled engine, a mixed gasoline/biofuel fueled engine, an alcohol fueled engine, a mixed gasoline/alcohol fueled engine, a compressed natural gas (CNG) fueled engine, or mixtures thereof. A diesel engine may be a compression-ignited engine. A gasoline engine may be a spark-ignited engine. An internal combustion engine may also be used in combination with an electrical or battery source of power. An engine so configured is commonly known as a hybrid engine. The internal combustion engine may be a 2-stroke, 4-stroke, or rotary engine. Suitable internal combustion engines include marine diesel engines (such as inland marine), aviation piston engines, low-load diesel engines, and motorcycle, automobile, locomotive, and truck engines. Engines may be coupled with a turbocharger.

The lubricating oil composition for an internal combustion engine may be suitable for any engine lubricant irrespective of the sulfur, phosphorus, or sulfated ash (ASTM D-874) content. The sulfur content of the engine oil lubricant may be about 1 wt. % or less, or about 0.8 wt. % or less, or about 0.5 wt. % or less, or about 0.3 wt. % or less, or about 0.2 wt. % or less. In one embodiment the sulfur content may be in the range of about 0.001 wt. % to about 0.5 wt. %, or about 0.01 wt. % to about 0.3 wt. %. The phosphorus content may be about 0.2 wt. % or less, or about 0.1 wt. % or less, or about 0.085 wt. % or less, or about 0.08 wt. % or less, or even about 0.06 wt. % or less, about 0.055 wt. % or less, or about 0.05 wt. % or less. In one embodiment, the phosphorus content may be about 50 ppm to about 1000 ppm, or about 325 ppm to about 850 ppm. The total sulfated ash content may be about 2 wt. % or less, or about 1.5 wt. % or less, or about 1.1 wt. % or less, or about 1 wt. % or less, or about 0.8 wt. % or less, or about 0.5 wt. % or less. In one embodiment the sulfated ash content may be about 0.05 wt. % to about 0.9 wt. %, or about 0.1 wt. % or about 0.2 wt. % to about 0.45 wt. %. In another embodiment, the sulfur content may be about 0.4 wt. % or less, the phosphorus content may be about 0.08 wt. % or less, and the sulfated ash is about 1 wt. % or less. In yet another embodiment the sulfur content may be about 0.3 wt. % or less, the phosphorus content is about 0.05 wt. % or less, and the sulfated ash may be about 0.8 wt. % or less.

Further, lubricants of the present description may be suitable to meet one or more industry specification requirements such as ILSAC GF-3, GF-4, GF-5, GF-6, PC-11, CF, CF-4, CH-4, CK-4, FA-4, CJ-4, CI-4 Plus, CI-4, API SG, SJ, SL, SM, SN, SN PLUS, ACEA A1/B1, A2/B2, A3/B3, A3/B4, A5/B5, A7/B7, C1, C2, C3, C4, C5, C6, E4/E6/E7/E9, Euro 5/6, JASO DL-1, Low SAPS, Mid SAPS, or original equipment manufacturer specifications such as Dexos1™, Dexos2™, MB-Approval 229.1, 229.3, 229.5, 229.51/229.31, 229.52, 229.6, 229.71, 226.5, 226.51, 228.0/.1, 228.2/.3, 228.31, 228.5, 228.51, 228.61, VW 501.01, 502.00, 503.00/503.01, 504.00, 505.00, 505.01, 506.00/506.01, 507.00, 508.00, 509.00, 508.88, 509.99, BMW Longlife-01, Longlife-01 FE, Longlife-04, Longlife-12 FE, Longlife-14 FE+, Longlife-17 FE+, Porsche A40, C30, Peugeot Citroën Automobiles B71 2290, B71 2294, B71 2295, B71 2296, B71 2297, B71 2300, B71 2302, B71 2312, B71 2007, B71 2008, Renault RN0700, RN0710, Ford WSS-M2C153-H, WSS-M2C930-A, WSS-M2C945-A, WSS-M2C913A, WSS-M2C913-B, WSS-M2C913-C, WSS-M2C913-D, WSS-M2C948-B, WSS-M2C948-A, GM 6094-M, Chrysler MS-6395, Fiat 9.55535 G1, G2, M2, N1, N2, Z2, S1, S2, S3, S4, T2, DS1, DSX, GH2, GS1, GSX, CR1, Jaguar Land Rover STJLR.03.5003, STJLR.03.5004, STJLR.03.5005, STJLR.03.5006, STJLR.03.5007, STJLR.51.5122 or any past or future PCMO or HDD specifications not mentioned herein. In some embodiments for passenger car motor oil (PCMO) applications, the amount of phosphorus in the finished fluid is 1000 ppm or less or 900 ppm or less or 800 ppm or less.

Base Oil or Base Oil Blend: The base oil used in the lubricating oil compositions herein may be oils of lubricating viscosity and selected from any of the base oils in Groups I-V as specified in the American Petroleum Institute (API) Base Oil Interchangeability Guidelines. The five base oil groups are generally set forth in Table 1 below:

TABLE 1

| Base oil Category | Sulfur (%) | | Saturates (%) | Viscosity Index |
|---|---|---|---|---|
| Group I | >0.03 | and/or | <90 | 80 to 120 |
| Group II | ≤0.03 | and | ≥90 | 80 to 120 |
| Group III | ≤0.03 | and | ≥90 | ≥120 |
| Group IV | All polyalphaolefins (PAOs) | | | |
| Group V | All others not included in Groups I, II, III, or IV | | | |

Groups I, II, and III are mineral oil process stocks. Group IV base oils contain true synthetic molecular species, which are produced by polymerization of olefinically unsaturated hydrocarbons. Many Group V base oils are also true synthetic products and may include diesters, polyol esters, polyalkylene glycols, alkylated aromatics, polyphosphate esters, polyvinyl ethers, and/or polyphenyl ethers, and the like, but may also be naturally occurring oils, such as vegetable oils. It should be noted that although Group III base oils are derived from mineral oil, the rigorous processing that these fluids undergo causes their physical properties to be very similar to some true synthetics, such as PAOs. Therefore, oils derived from Group III base oils may be referred to as synthetic fluids in the industry. Group II+ may comprise high viscosity index Group II.

The base oil blend used in the disclosed lubricating oil composition may be a mineral oil, animal oil, vegetable oil, synthetic oil, synthetic oil blends, or mixtures thereof. Suitable oils may be derived from hydrocracking, hydrogenation, hydrofinishing, unrefined, refined, and re-refined oils, and mixtures thereof.

Unrefined oils are those derived from a natural, mineral, or synthetic source without or with little further purification treatment. Refined oils are similar to the unrefined oils except that they have been treated in one or more purification steps, which may result in the improvement of one or more properties. Examples of suitable purification techniques are solvent extraction, secondary distillation, acid or base extraction, filtration, percolation, and the like. Oils refined to the quality of an edible may or may not be useful. Edible oils may also be called white oils. In some embodiments, lubricating oil compositions are free of edible or white oils.

Re-refined oils are also known as reclaimed or reprocessed oils. These oils are obtained similarly to refined oils using the same or similar processes. Often these oils are additionally processed by techniques directed to removal of spent additives and oil breakdown products.

Mineral oils may include oils obtained by drilling or from plants and animals or any mixtures thereof. For example, such oils may include, but are not limited to, castor oil, lard oil, olive oil, peanut oil, corn oil, soybean oil, and linseed oil, as well as mineral lubricating oils, such as liquid petroleum oils and solvent-treated or acid-treated mineral lubricating oils of the paraffinic, naphthenic or mixed paraffinic-naphthenic types. Such oils may be partially or fully hydrogenated, if desired. Oils derived from coal or shale may also be useful.

Useful synthetic lubricating oils may include hydrocarbon oils such as polymerized, oligomerized, or interpolymerized olefins (e.g., polybutylenes, polypropylenes, propyleneisobutylene copolymers); poly(1-hexenes), poly(1-octenes), trimers or oligomers of 1-decene, e.g., poly(1-decenes), such materials being often referred to as α-olefins, and mixtures thereof; alkyl-benzenes (e.g. dodecylbenzenes, tetradecylbenzenes, dinonylbenzenes, di-(2-ethylhexyl)-benzenes); polyphenyls (e.g., biphenyls, terphenyls, alkylated polyphenyls); diphenyl alkanes, alkylated diphenyl alkanes, alkylated diphenyl ethers and alkylated diphenyl sulfides and the derivatives, analogs and homologs thereof or mixtures thereof. Polyalphaolefins are typically hydrogenated materials.

Other synthetic lubricating oils include polyol esters, diesters, liquid esters of phosphorus-containing acids (e.g., tricresyl phosphate, trioctyl phosphate, and the diethyl ester of decane phosphonic acid), or polymeric tetrahydrofurans. Synthetic oils may be produced by Fischer-Tropsch reactions and typically may be hydroisomerized Fischer-Tropsch hydrocarbons or waxes. In one embodiment oils may be prepared by a Fischer-Tropsch gas-to-liquid synthetic procedure as well as other gas-to-liquid oils.

The major amount of base oil included in a lubricating composition may be selected from the group consisting of Group I, Group II, a Group III, a Group IV, a Group V, and a combination of two or more of the foregoing, and wherein the major amount of base oil is other than base oils that arise from provision of additive components or viscosity index improvers in the composition. In another embodiment, the major amount of base oil included in a lubricating composition may be selected from the group consisting of Group II, a Group III, a Group IV, a Group V, and a combination of two or more of the foregoing, and wherein the major amount of base oil is other than base oils that arise from provision of additive components or viscosity index improvers in the composition.

The amount of the oil of lubricating viscosity present may be the balance remaining after subtracting from 100 wt. % the sum of the amount of the performance additives inclusive of viscosity index improver(s) and/or pour point depressant(s) and/or other top treat additives. For example, the oil of lubricating viscosity that may be present in a finished fluid may be a major amount, such as greater than about 50 wt. %, greater than about 60 wt. %, greater than about 70 wt. %, greater than about 80 wt. %, greater than about 85 wt. %, or greater than about 90 wt. %.

Optional Additives:The lubricating oil compositions herein may also include a number of optional additives combined with the optionally overbased and sulfurized alkyl phenate product as needed to meet performance standards. Those optional additives are described in the following paragraphs.

Dispersants: The lubricating oil composition may optionally include one or more dispersants or mixtures thereof. Dispersants are often known as ashless-type dispersants because, prior to mixing in a lubricating oil composition, they do not contain ash-forming metals and they do not normally contribute any ash when added to a lubricant. Ashless type dispersants are characterized by a polar group attached to a relatively high molecular weight hydrocarbon chain. Typical ashless dispersants include N-substituted long chain alkenyl succinimides. Examples of N-substituted long chain alkenyl succinimides include polyisobutylene succinimide with the number average molecular weight of the polyisobutylene substituent being in the range about 350 to about 50,000, or to about 5,000, or to about 3,000, as measured by GPC. Succinimide dispersants and their preparation are disclosed, for instance in U.S. Pat. No. 7,897,696 or U.S. Pat. No. 4,234,435. The alkenyl substituent may be prepared from polymerizable monomers containing about 2 to about 16, or about 2 to about 8, or about 2 to about 6 carbon atoms. Succinimide dispersants are typically the imide formed from a polyamine, typically a poly(ethyleneamine).

Preferred amines are selected from polyamines and hydroxyamines. Examples of polyamines that may be used include, but are not limited to, diethylene triamine (DETA), triethylene tetramine (TETA), tetraethylene pentamine (TEPA), and higher homologues such as pentaethylamine hexamine (PEHA), and the like.

A suitable heavy polyamine is a mixture of polyalkylenepolyamines comprising small amounts of lower polyamine oligomers such as TEPA and PEHA (pentaethylene hexamine) but primarily oligomers with 6 or more nitrogen atoms, 2 or more primary amines per molecule, and more extensive branching than conventional polyamine mixtures. A heavy polyamine preferably includes polyamine oligomers containing 7 or more nitrogens per molecule and with 2 or more primary amines per molecule. The heavy polyamine comprises more than 28 wt. % (e.g., >32 wt. %) total nitrogen and an equivalent weight of primary amine groups of 120-160 grams per equivalent.

In some approaches, suitable polyamines are commonly known as PAM and contain a mixture of ethylene amines where TEPA and pentaethylene hexamine (PEHA) are the major part of the polyamine, usually less than about 80%.

Typically, PAM has 8.7-8.9 milliequivalents of primary amine per gram (an equivalent weight of 115 to 112 grams per equivalent of primary amine) and a total nitrogen content of about 33-34 wt. %. Heavier cuts of PAM oligomers with practically no TEPA and only very small amounts of PEHA but containing primarily oligomers with more than 6 nitrogens and more extensive branching, may produce dispersants with improved dispersancy.

In an embodiment the present disclosure further comprises at least one polyisobutylene succinimide dispersant derived from polyisobutylene with a number average molecular weight in the range about 350 to about 50,000, or to about 5000, or to about 3000, as determined by GPC. The polyisobutylene succinimide may be used alone or in combination with other dispersants.

In some embodiments, polyisobutylene, when included, may have greater than 50 mol %, greater than 60 mol %, greater than 70 mol %, greater than 80 mol %, or greater than 90 mol % content of terminal double bonds. Such PIB is also referred to as highly reactive PIB ("HR-PIB"). HR-PIB having a number average molecular weight ranging from about 800 to about 5000, as determined by GPC, is suitable for use in embodiments of the present disclosure. Conventional PIB typically has less than 50 mol %, less than 40 mol %, less than 30 mol %, less than 20 mol %, or less than 10 mol % content of terminal double bonds.

An HR-PIB having a number average molecular weight ranging from about 900 to about 3000 may be suitable, as determined by GPC. Such HR-PIB is commercially available, or can be synthesized by the polymerization of isobutene in the presence of a non-chlorinated catalyst such as boron trifluoride, as described in U.S. Pat. No. 4,152,499 to Boerzel, et al. and U.S. Pat. No. 5,739,355 to Gateau, et al. When used in the aforementioned thermal ene reaction, HR-PIB may lead to higher conversion rates in the reaction, as well as lower amounts of sediment formation, due to increased reactivity. A suitable method is described in U.S. Pat. No. 7,897,696.

In one embodiment, the present disclosure further comprises at least one dispersant derived from polyisobutylene succinic anhydride ("PIBSA"). The PIBSA may have an average of between about 1.0 and about 2.0 succinic acid moieties per polymer.

The % actives of the alkenyl or alkyl succinic anhydride can be determined using a chromatographic technique. This method is described in column 5 and 6 in U.S. Pat. No. 5,334,321.

The percent conversion of the polyolefin is calculated from the % actives using the equation in column 5 and 6 in U.S. Pat. No. 5,334,321.

Unless stated otherwise, all percentages are in weight percent and all molecular weights are number average molecular weights determined by gel permeation chromatography (GPC) using commercially available polystyrene standards (with a number average molecular weight of 180 to about 18,000 as the calibration reference).

In one embodiment, the dispersant may be derived from a polyalphaolefin (PAO) succinic anhydride. In one embodiment, the dispersant may be derived from olefin maleic anhydride copolymer. As an example, the dispersant may be described as a poly-PIBSA. In an embodiment, the dispersant may be derived from an anhydride which is grafted to an ethylene-propylene copolymer.

A suitable class of nitrogen-containing dispersants may be derived from olefin copolymers (OCP), more specifically, ethylene-propylene dispersants which may be grafted with maleic anhydride. A more complete list of nitrogen-containing compounds that can be reacted with the functionalized OCP are described in U.S. Pat. Nos. 7,485,603; 7,786,057; 7,253,231; 6,107,257; and 5,075,383; and/or are commercially available.

One class of suitable dispersants may also be Mannich bases. Mannich bases are materials that are formed by the condensation of a higher molecular weight, alkyl substituted phenol, a polyalkylene polyamine, and an aldehyde such as formaldehyde. Mannich bases are described in more detail in U.S. Pat. No. 3,634,515.

A suitable class of dispersants may also be high molecular weight esters or half ester amides. A suitable dispersant may also be post-treated by conventional methods by a reaction with any of a variety of agents. Among these are boron, urea, thiourea, dimercaptothiadiazoles, carbon disulfide, aldehydes, ketones, carboxylic acids, hydrocarbon-substituted succinic anhydrides, maleic anhydride, nitriles, epoxides, carbonates, cyclic carbonates, hindered phenolic esters, and phosphorus compounds. U.S. Pat. Nos. 7,645,726; 7,214,649; and 8,048,831 are incorporated herein by reference in their entireties.

In addition to the carbonate and boric acids post-treatments both the compounds may be post-treated, or further post-treatment, with a variety of post-treatments designed to improve or impart different properties. Such post-treatments include those summarized in columns 27-29 of U.S. Pat. No. 5,241,003, hereby incorporated by reference. Such treatments include, treatment with: Inorganic phosphorous acids or anhydrates (e.g., U.S. Pat. Nos. 3,403,102 and 4,648,980); Organic phosphorous compounds (e.g., U.S. Pat. No. 3,502,677); Phosphorous pentasulfides; Boron compounds as already noted above (e.g., U.S. Pat. Nos. 3,178,663 and 4,652,387); Carboxylic acid, polycarboxylic acids, anhydrides and/or acid halides (e.g., U.S. Pat. Nos. 3,708,522 and 4,948,386); Epoxides polyepoxiates or thioexpoxides (e.g., U.S. Pat. Nos. 3,859,318 and 5,026,495); Aldehyde or ketone (e.g., U.S. Pat. No. 3,458,530); Carbon disulfide (e.g., U.S. Pat. No. 3,256,185); Glycidol (e.g., U.S. Pat. No. 4,617,137); Urea, thiourea or guanidine (e.g., U.S. Pat. Nos. 3,312,619; 3,865,813; and British Patent GB 1,065,595); Organic sulfonic acid (e.g., U.S. Pat. No. 3,189,544 and British Patent GB 2,140,811); Alkenyl cyanide (e.g., U.S. Pat. Nos. 3,278,550 and 3,366,569); Diketene (e.g., U.S. Pat. No. 3,546,243); A diisocyanate (e.g., U.S. Pat. No. 3,573,205); Alkane sultone (e.g., U.S. Pat. No. 3,749,695); 1,3-Dicarbonyl Compound (e.g., U.S. Pat. No. 4,579,675); Sulfate of alkoxylated alcohol or phenol (e.g., U.S. Pat. No. 3,954,639); Cyclic lactone (e.g., U.S. Pat. Nos. 4,617,138; 4,645,515; 4,668,246; 4,963,275; and 4,971,711); Cyclic carbonate or thiocarbonate linear monocarbonate or polycarbonate, or chloroformate (e.g., U.S. Pat. Nos. 4,612,132; 4,647,390; 4,648,886; 4,670,170); Nitrogen-containing carboxylic acid (e.g., U.S. Pat. No. 4,971,598 and British Patent GB 2,140,811); Hydroxy-protected chlorodicarbonyloxy compound (e.g., U.S. Pat. No. 4,614,522); Lactam, thiolactam, thiolactone or dithiolactone (e.g., U.S. Pat. Nos. 4,614,603 and 4,666,460); Cyclic carbonate or thiocarbonate, linear monocarbonate or polycarbonate, or chloroformate (e.g., U.S. Pat. Nos. 4,612,132; 4,647,390; 4,646,860; and 4,670,170); Nitrogen-containing carboxylic acid (e.g., U.S. Pat. No. 4,971,598 and British Patent GB 2,440,811); Hydroxy-protected chlorodicarbonyloxy compound (e.g., U.S. Pat. No. 4,614,522); Lactam, thiolactam, thiolactone or dithiolactone (e.g., U.S. Pat. Nos. 4,614,603, and 4,666, 460); Cyclic carbamate, cyclic thiocarbamate or cyclic dithiocarbamate (e.g., U.S. Pat. Nos. 4,663,062 and 4,666,459); Hydroxyaliphatic carboxylic acid (e.g., U.S. Pat. Nos. 4,482, 464; 4,521,318; 4,713,189); Oxidizing agent (e.g., U.S. Pat. No. 4,379,064); Combination of phosphorus pentasulfide and a polyalkylene polyamine (e.g., U.S. Pat. No. 3,185, 647); Combination of carboxylic acid or an aldehyde or ketone and sulfur or sulfur chloride (e.g., U.S. Pat. Nos. 3,390,086; 3,470,098); Combination of a hydrazine and carbon disulfide (e.g. U.S. Pat. No. 3,519,564); Combination of an aldehyde and a phenol (e.g., U.S. Pat. Nos. 3,649,229; 5,030,249; 5,039,307); Combination of an aldehyde and an O-diester of dithiophosphoric acid (e.g., U.S. Pat. No. 3,865, 740); Combination of a hydroxyaliphatic carboxylic acid and a boric acid (e.g., U.S. Pat. No. 4,554,086); Combination of a hydroxyaliphatic carboxylic acid, then formaldehyde and a phenol (e.g., U.S. Pat. No. 4,636,322); Combination of a hydroxyaliphatic carboxylic acid and then an aliphatic dicarboxylic acid (e.g., U.S. Pat. No. 4,663,064); Combination of formaldehyde and a phenol and then glycolic acid (e.g., U.S. Pat. No. 4,699,724); Combination of a hydroxyaliphatic carboxylic acid or oxalic acid and then a diisocyanate (e.g. U.S. Pat. No. 4,713,191); Combination of inorganic acid or anhydride of phosphorus or a partial or total sulfur analog thereof and a boron compound (e.g., U.S. Pat. No. 4,857,214); Combination of an organic diacid then an unsaturated fatty acid and then a nitrosoaromatic amine optionally followed by a boron compound and then a glycolating agent (e.g., U.S. Pat. No. 4,973,412); Combination of an aldehyde and a triazole (e.g., U.S. Pat. No. 4,963,278); Combination of an aldehyde and a triazole then a boron compound (e.g., U.S. Pat. No. 4,981,492); Combination of cyclic lactone and a boron compound (e.g., U.S. Pat. Nos. 4,963,275 and 4,971,711). The above-mentioned patents are herein incorporated in their entireties.

The TBN of a suitable dispersant may be from about 10 to about 65 mg KOH/g dispersant, on an oil-free basis, which is comparable to about 5 to about 30 TBN if measured on a dispersant sample containing about 50% diluent oil. TBN is measured by the method of ASTM D2896.

In yet other embodiments, the optional dispersant additive may be a hydrocarbyl substituted succinamide or succinimide dispersant. In approaches, the hydrocarbyl substituted succinamide or succinimide dispersant may be derived from a hydrocarbyl substituted acylating agent reacted with a polyalkylene polyamine and wherein the hydrocarbyl substituent of the succinamide or the succinimide dispersant is a linear or branched hydrocarbyl group having a number average molecular weight of about 250 to about 5,000 as measured by GPC using polystyrene as a calibration reference.

In some approaches, the polyalkylene polyamine used to form the dispersant has the Formula

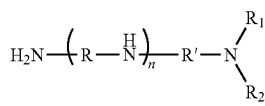

wherein each R and R', independently, is a divalent C1 to C6 alkylene linker, each $R_1$ and $R_2$, independently, is hydrogen, a C1 to C6 alkyl group, or together with the nitrogen atom to which they are attached form a 5- or 6-membered ring optionally fused with one or more aromatic or non-aromatic rings, and n is an integer from 0 to 8. In other approaches, the polyalkylene polyamine is selected from the group consisting of a mixture of polyethylene polyamines having an average of 5 to 7 nitrogen atoms, triethylenetetramine, tetraethylenepentamine, and combinations thereof.

The dispersant, if present, can be used in an amount sufficient to provide up to about 20 wt. %, based upon the final weight of the lubricating oil composition. Another amount of the dispersant that can be used may be about 0.1 wt. % to about 15 wt. %, or about 0.1 wt. % to about 10 wt. %, about 0.1 to 8 wt. %, or about 1 wt. % to about 10 wt. %, or about 1 wt. % to about 8 wt. %, or about 1 wt. % to about 6 wt. %, based upon the final weight of the lubricating oil composition. In some embodiments, the lubricating oil composition utilizes a mixed dispersant system. A single type or a mixture of two or more types of dispersants in any desired ratio may be used.

Antioxidants: The lubricating oil compositions herein also may optionally contain one or more antioxidants. Antioxidant compounds are known and include for example, phenates, phenate sulfides, sulfurized olefins, phosphosulfurized terpenes, sulfurized esters, aromatic amines, alkylated diphenylamines (e.g., nonyl diphenylamine, di-nonyl diphenylamine, octyl diphenylamine, di-octyl diphenylamine), phenyl-alpha-naphthyl amines, alkylated phenyl-alpha-naphthylamines, hindered non-aromatic amines, phenols, hindered phenols, oil-soluble molybdenum compounds, macromolecular antioxidants, or mixtures thereof. Antioxidant compounds may be used alone or in combination.

The hindered phenol antioxidant may contain a secondary butyl and/or a tertiary butyl group as a sterically hindering group. The phenol group may be further substituted with a hydrocarbyl group and/or a bridging group linking to a second aromatic group. Examples of suitable hindered phenol antioxidants include 2,6-di-tert-butylphenol, 4-methyl-2,6-di-tert-butylphenol, 4-ethyl-2,6-di-tert-butylphenol, 4-propyl-2,6-di-tert-butylphenol or 4-butyl-2,6-di-tert-butylphenol, or 4-dodecyl-2,6-di-tert-butylphenol. In one embodiment the hindered phenol antioxidant may be an ester and may include, e.g., Irganox™ L-135 available from BASF or an addition product derived from 2,6-di-tert-butylphenol and an alkyl acrylate, wherein the alkyl group may contain about 1 to about 18, or about 2 to about 12, or about 2 to about 8, or about 2 to about 6, or about 4 carbon atoms. Another commercially available hindered phenol antioxidant may be an ester and may include Ethanox™ 4716 available from Albemarle Corporation.

Useful antioxidants may include diarylamines and high molecular weight phenols. In an embodiment, the lubricating oil composition may contain a mixture of a diarylamine and a high molecular weight phenol, such that each antioxidant may be present in an amount sufficient to provide up to about 5%, by weight, based upon the final weight of the lubricating oil composition. In an embodiment, the antioxidant may be a mixture of about 0.3 to about 1.5% diarylamine and about 0.4 to about 2.5% high molecular weight phenol, by weight, based upon the final weight of the lubricating oil composition.

Examples of suitable olefins that may be sulfurized to form a sulfurized olefin include propylene, butylene, isobutylene, polyisobutylene, pentene, hexene, heptene, octene, nonene, decene, undecene, dodecene, tridecene, tetradecene, pentadecene, hexadecene, heptadecene, octadecene, nonadecene, eicosene or mixtures thereof. In one embodiment, hexadecene, heptadecene, octadecene, nonadecene, eicosene or mixtures thereof and their dimers, trimers and tetramers are especially useful olefins. Alternatively, the olefin may be a Diels-Alder adduct of a diene such as 1,3-butadiene and an unsaturated ester, such as, butylacrylate.

Another class of sulfurized olefin includes sulfurized fatty acids and their esters. The fatty acids are often obtained from vegetable oil or animal oil and typically contain about 4 to about 22 carbon atoms. Examples of suitable fatty acids and their esters include triglycerides, oleic acid, linoleic acid, palmitoleic acid or mixtures thereof. Often, the fatty acids are obtained from lard oil, tall oil, peanut oil, soybean oil, cottonseed oil, sunflower seed oil or mixtures thereof. Fatty acids and/or ester may be mixed with olefins, such as α-olefins.

In another alternative embodiment the antioxidant composition also contains a molybdenum-containing antioxidant in addition to the phenolic and/or aminic antioxidants discussed above. When a combination of these three antioxidants is used, preferably the ratio of phenolic to aminic to molybdenum-containing is (0 to 2):(0 to 2):(0 to 1).

The one or more antioxidant(s) may be present in ranges about 0 wt. % to about 20 wt. %, or about 0.1 wt. % to about 10 wt. %, or about 1 wt. % to about 5 wt. %, of the lubricating oil composition.

Antiwear Agents: The lubricating oil compositions herein also may optionally contain one or more antiwear agents. Examples of suitable antiwear agents include, but are not limited to, a metal thiophosphate; a metal dialkyldithiophosphate; a phosphoric acid ester or salt thereof; a phosphate ester(s); a phosphite; a phosphorus-containing carboxylic ester, ether, or amide; a sulfurized olefin; thiocarbamate-containing compounds including, thiocarbamate esters, alkylene-coupled thiocarbamates, and bis(S-alkyldithiocarbamyl)disulfides; and mixtures thereof. A suitable antiwear agent may be a molybdenum dithiocarbamate. The phosphorus containing antiwear agents are more fully described in European Patent 612 839. The metal in the dialkyl dithio phosphate salts may be an alkali metal, alkaline earth metal, aluminum, lead, tin, molybdenum, manganese, nickel, copper, titanium, or zinc. A useful antiwear agent may be zinc dialkyldithiophosphate.

Further examples of suitable antiwear agents include titanium compounds, tartrates, tartrimides, oil soluble amine salts of phosphorus compounds, sulfurized olefins, phosphites (such as dibutyl phosphite), phosphonates, thiocarbamate-containing compounds, such as thiocarbamate esters, thiocarbamate amides, thiocarbamic ethers, alkylene-coupled thiocarbamates, and bis(S-alkyldithiocarbamyl) disulfides. The tartrate or tartrimide may contain alkyl-ester groups, where the sum of carbon atoms on the alkyl groups may be at least 8. The antiwear agent may in one embodiment include a citrate.

The antiwear agent may be present in ranges including about 0 wt. % to about 15 wt. %, or about 0.01 wt. % to about 10 wt. %, or about 0.05 wt. % to about 5 wt. %, or about 0.1 wt. % to about 3 wt. % of the lubricating oil composition.

Boron-Containing Compounds: The lubricating oil compositions herein may optionally contain one or more boron-containing compounds. Examples of boron-containing compounds include borate esters, borated fatty amines, borated epoxides, borated detergents, and borated dispersants, such as borated succinimide dispersants, as disclosed in U.S. Pat. No. 5,883,057. The boron-containing compound, if present, can be used in an amount sufficient to provide up to about 8 wt. %, about 0.01 wt. % to about 7 wt. %, about 0.05 wt. % to about 5 wt. %, or about 0.1 wt. % to about 3 wt. % of the lubricating oil composition.

Additional Detergents: The lubricating oil composition may optionally further comprise one or more neutral, low based, or overbased detergents, and mixtures thereof. Suitable detergent substrates include phenates, sulfur containing phenates, sulfonates, calixarates, salixarates, salicylates, carboxylic acids, phosphorus acids, mono- and/or di-thiophosphoric acids, alkyl phenols, sulfur coupled alkyl phenol compounds, or methylene bridged phenols. Suitable detergents and their methods of preparation are described in greater detail in numerous patent publications, including U.S. Pat. No. 7,732,390 and references cited therein.

The detergent substrate may be salted with an alkali or alkaline earth metal such as, but not limited to, calcium, magnesium, potassium, sodium, lithium, barium, or mixtures thereof. In some embodiments, the detergent is free of barium. In some embodiments, a detergent may contain traces of other metals such as magnesium or calcium in amounts such as 50 ppm or less, 40 ppm or less, 30 ppm or less, 20 ppm or less, or 10 ppm or less. A suitable detergent may include alkali or alkaline earth metal salts of petroleum sulfonic acids and long chain mono- or di-alkylarylsulfonic acids with the aryl group being benzyl, tolyl, and xylyl. Examples of suitable detergents include, but are not limited to, calcium phenates, calcium sulfur containing phenates, calcium sulfonates, calcium calixarates, calcium salixarates, calcium salicylates, calcium carboxylic acids, calcium phosphorus acids, calcium mono- and/or di-thiophosphoric acids, calcium alkyl phenols, calcium sulfur coupled alkyl phenol compounds, calcium methylene bridged phenols, magnesium phenates, magnesium sulfur containing phenates, magnesium sulfonates, magnesium calixarates, magnesium salixarates, magnesium salicylates, magnesium carboxylic acids, magnesium phosphorus acids, magnesium mono- and/or di-thiophosphoric acids, magnesium alkyl phenols, magnesium sulfur coupled alkyl phenol compounds, magnesium methylene bridged phenols, sodium phenates, sodium sulfur containing phenates, sodium sulfonates, sodium calixarates, sodium salixarates, sodium salicylates, sodium carboxylic acids, sodium phosphorus acids, sodium mono- and/or di-thiophosphoric acids, sodium alkyl phenols, sodium sulfur coupled alkyl phenol compounds, or sodium methylene bridged phenols.

Overbased detergent additives are well known in the art and may be alkali or alkaline earth metal overbased detergent additives. Such detergent additives may be prepared by reacting a metal oxide or metal hydroxide with a substrate and carbon dioxide gas. The substrate is typically an acid, for example, an acid such as an aliphatic substituted sulfonic acid, an aliphatic substituted carboxylic acid, or an aliphatic substituted phenol.

The terminology "overbased" relates to metal salts, such as metal salts of sulfonates, carboxylates, and phenates, wherein the amount of metal present exceeds the stoichiometric amount. Such salts may have a conversion level in excess of 100% (i.e., they may comprise more than 100% of the theoretical amount of metal needed to convert the acid to its "normal," "neutral" salt). The expression "metal ratio," often abbreviated as MR, is used to designate the ratio of total chemical equivalents of metal in the overbased salt to chemical equivalents of the metal in a neutral salt according to known chemical reactivity and stoichiometry. In a normal or neutral salt, the metal ratio is one and in an overbased salt, MR, is greater than one. They are commonly referred to as overbased, hyperbased, or superbased salts and may be salts of organic sulfur acids, carboxylic acids, or phenols.

An overbased detergent of the lubricating oil composition may have a total base number (TBN) of about 200 mg KOH/gram or greater, or as further examples, about 250 mg KOH/gram or greater, or about 350 mg KOH/gram or greater, or about 375 mg KOH/gram or greater, or about 400 mg KOH/gram or greater. The TBN being measured by the method of ASTM D-2896.

Examples of suitable overbased detergents include, but are not limited to, overbased calcium phenates, overbased calcium sulfur containing phenates, overbased calcium sulfonates, overbased calcium calixarates, overbased calcium salixarates, overbased calcium salicylates, overbased calcium carboxylic acids, overbased calcium phosphorus acids, overbased calcium mono- and/or di-thiophosphoric acids, overbased calcium alkyl phenols, overbased calcium sulfur coupled alkyl phenol compounds, overbased calcium methylene bridged phenols, overbased magnesium phenates, overbased magnesium sulfur containing phenates, overbased magnesium sulfonates, overbased magnesium calixarates, overbased magnesium salixarates, overbased magnesium salicylates, overbased magnesium carboxylic acids, overbased magnesium phosphorus acids, overbased magnesium mono- and/or di-thiophosphoric acids, overbased magnesium alkyl phenols, overbased magnesium sulfur coupled alkyl phenol compounds, or overbased magnesium methylene bridged phenols.

The overbased calcium phenate detergents have a total base number of at least about 150 mg KOH/g, at least about 225 mg KOH/g, at least about 225 mg KOH/g to about 400 mg KOH/g, at least about 225 mg KOH/g to about 350 mg KOH/g or about 230 mg KOH/g to about 350 mg KOH/g, all as measured by the method of ASTM D-2896. When such detergent compositions are formed in an inert diluent, e.g., a process oil, usually a mineral oil, the total base number reflects the basicity of the overall composition including diluent, and any other materials (e.g., promoter, etc.) that may be contained in the detergent composition.

The overbased detergent may have a metal to substrate ratio of from 1.1:1, or from 2:1, or from 4:1, or from 5:1, or from 7:1, or from 10:1. In some embodiments, a detergent is effective at reducing or preventing rust in an engine or other automotive part such as a transmission or gear. The detergent may be present in a lubricating composition at about 0 wt. % to about 10 wt. %, or about 0.1 wt. % to about 8 wt. %, or about 1 wt. % to about 4 wt. %, or greater than about 4 wt. % to about 8 wt. %.

Extreme Pressure Agents: The lubricating oil compositions herein also may optionally contain one or more extreme pressure agents. Extreme Pressure (EP) agents that are soluble in the oil include sulfur- and chlorosulfur-containing EP agents, chlorinated hydrocarbon EP agents and phosphorus EP agents. Examples of such EP agents include chlorinated wax; organic sulfides and polysulfides such as dibenzyldisulfide, bis(chlorobenzyl) disulfide, dibutyl tetrasulfide, sulfurized methyl ester of oleic acid, sulfurized alkyl phenol, sulfurized dipentene, sulfurized terpene, and sulfurized Diels-Alder adducts; phosphosulfurized hydrocarbons such as the reaction product of phosphorus sulfide with turpentine or methyl oleate; phosphorus esters such as the dihydrocarbyl and trihydrocarbyl phosphites, e.g., dibutyl phosphite, diheptyl phosphite, dicyclohexyl phosphite, pentylphenyl phosphite; dipentylphenyl phosphite, tridecyl phosphite, distearyl phosphite and polypropylene substituted phenyl phosphite; metal thiocarbamates such as zinc dioctyldithiocarbamate and barium heptylphenol diacid; amine salts of alkyl and dialkylphosphoric acids, including, for example, the amine salt of the reaction product of a dialkyldithiophosphoric acid with propylene oxide; and mixtures thereof.

Friction Modifiers: The lubricating oil compositions herein also may optionally contain one or more friction modifiers. Suitable friction modifiers may comprise metal containing and metal-free friction modifiers and may include, but are not limited to, imidazolines, amides, amines, succinimides, alkoxylated amines, alkoxylated ether amines, amine oxides, amidoamines, nitriles, betaines, quaternary amines, imines, amine salts, amino guanadine, alkanolamides, phosphonates, metal-containing compounds, glycerol esters, sulfurized fatty compounds and olefins, sunflower oil other naturally occurring plant or animal oils, dicarboxylic acid esters, esters or partial esters of a polyol and one or more aliphatic or aromatic carboxylic acids, and the like.

Suitable friction modifiers may contain hydrocarbyl groups that are selected from straight chain, branched chain, or aromatic hydrocarbyl groups or mixtures thereof, and may be saturated or unsaturated. The hydrocarbyl groups may be composed of carbon and hydrogen or hetero atoms such as sulfur or oxygen. The hydrocarbyl groups may range from about 12 to about 25 carbon atoms. In some embodiments the friction modifier may be a long chain fatty acid ester. In another embodiment the long chain fatty acid ester may be a mono-ester, or a di-ester, or a (tri)glyceride. The friction modifier may be a long chain fatty amide, a long chain fatty ester, a long chain fatty epoxide derivatives, or a long chain imidazoline.

Other suitable friction modifiers may include organic, ashless (metal-free), nitrogen-free organic friction modifiers. Such friction modifiers may include esters formed by reacting carboxylic acids and anhydrides with alkanols and generally include a polar terminal group (e.g., carboxyl or hydroxyl) covalently bonded to an oleophilic hydrocarbon chain. An example of an organic ashless nitrogen-free friction modifier is known generally as glycerol monooleate (GMO) which may contain mono-, di-, and tri-esters of oleic acid. Other suitable friction modifiers are described in U.S. Pat. No. 6,723,685, herein incorporated by reference in its entirety.

Aminic friction modifiers may include amines or polyamines. Such compounds can have hydrocarbyl groups that are linear, either saturated or unsaturated, or a mixture thereof and may contain from about 12 to about 25 carbon atoms. Further examples of suitable friction modifiers include alkoxylated amines and alkoxylated ether amines. Such compounds may have hydrocarbyl groups that are linear, either saturated, unsaturated, or a mixture thereof. They may contain from about 12 to about 25 carbon atoms. Examples include ethoxylated amines and ethoxylated ether amines.

The amines and amides may be used as such or in the form of an adduct or reaction product with a boron compound such as a boric oxide, boron halide, metaborate, boric acid or a mono-, di- or tri-alkyl borate. Other suitable friction modifiers are described in U.S. Pat. No. 6,300,291, herein incorporated by reference in its entirety.

A friction modifier may optionally be present in ranges such as about 0 wt. % to about 10 wt. %, or about 0.01 wt. % to about 8 wt. %, or about 0.1 wt. % to about 4 wt. %.

Molybdenum-containing component: The lubricating oil compositions herein also may optionally contain one or more molybdenum-containing compounds. An oil-soluble molybdenum compound may have the functional performance of an antiwear agent, an antioxidant, a friction modifier, or mixtures thereof. An oil-soluble molybdenum compound may include molybdenum dithiocarbamates, molybdenum dialkyldithiophosphates, molybdenum dithiophosphinates, amine salts of molybdenum compounds, molybdenum xanthates, molybdenum thioxanthates, molybdenum sulfides, molybdenum carboxylates, molybdenum alkoxides, a trinuclear organo-molybdenum compound, and/or mixtures thereof. The molybdenum sulfides include molybdenum disulfide. The molybdenum disulfide may be in the form of a stable dispersion. In one embodiment the oil-soluble molybdenum compound may be selected from the group consisting of molybdenum dithiocarbamates, molybdenum dialkyldithiophosphates, amine salts of molybdenum compounds, and mixtures thereof. In one embodiment the oil-soluble molybdenum compound may be a molybdenum dithiocarbamate.

Suitable examples of molybdenum compounds which may be used include commercial materials sold under the trade names such as Molyvan 822™, Molyvan™ A, Molyvan 2000™ and Molyvan 855™ from R. T. Vanderbilt Co., Ltd., and Sakura-Lube™ S-165, S-200, S-300, S-310G, S-525, S-600, S-700, and S-710 available from Adeka Corporation, and mixtures thereof. Suitable molybdenum components are described in U.S. Pat. No. 5,650,381; US RE 37,363 E1; US RE 38,929 E1; and US RE 40,595 E1, incorporated herein by reference in their entireties.

Additionally, the molybdenum compound may be an acidic molybdenum compound. Included are molybdic acid, ammonium molybdate, sodium molybdate, potassium molybdate, and other alkaline metal molybdates and other molybdenum salts, e.g., hydrogen sodium molybdate, MoOCl4, MoO2Br2, Mo2O3Cl6, molybdenum trioxide or similar acidic molybdenum compounds. Alternatively, the compositions can be provided with molybdenum by molybdenum/sulfur complexes of basic nitrogen compounds as described, for example, in U.S. Pat. Nos. 4,263,152; 4,285,822; 4,283,295; 4,272,387; 4,265,773; 4,261,843; 4,259,195 and 4,259,194; and WO 94/06897, incorporated herein by reference in their entireties.

Another class of suitable organo-molybdenum compounds are trinuclear molybdenum compounds, such as those of the formula Mo3 SkLnQz and mixtures thereof, wherein S represents sulfur, L represents independently selected ligands having organo groups with a sufficient number of carbon atoms to render the compound soluble or dispersible in the oil, n is from 1 to 4, k varies from 4 through 7, Q is selected from the group of neutral electron donating compounds such as water, amines, alcohols, phosphines, and ethers, and z ranges from 0 to 5 and includes non-stoichiometric values. At least 21 total carbon atoms may be present among all the ligands' organo groups, such as at least 25, at least 30, or at least 35 carbon atoms. Additional suitable molybdenum compounds are described in U.S. Pat. No. 6,723,685, herein incorporated by reference in its entirety.

The oil-soluble molybdenum compound may be present in an amount sufficient to provide about 0.5 ppm to about 2000 ppm, about 1 ppm to about 700 ppm, about 1 ppm to about 550 ppm, about 5 ppm to about 300 ppm, or about 20 ppm to about 250 ppm of molybdenum.

Transition Metal-containing compounds: In another embodiment, the oil-soluble compound may be a transition metal containing compound or a metalloid. The transition metals may include, but are not limited to, titanium, vanadium, copper, zinc, zirconium, molybdenum, tantalum, tungsten, and the like. Suitable metalloids include, but are not limited to, boron, silicon, antimony, tellurium, and the like.

In an embodiment, an oil-soluble transition metal-containing compound may function as antiwear agents, friction modifiers, antioxidants, deposit control additives, or more than one of these functions. In an embodiment the oil-soluble transition metal-containing compound may be an oil-soluble titanium compound, such as a titanium (IV) alkoxide. Among the titanium containing compounds that may be used in, or which may be used for preparation of the oils-soluble materials of, the disclosed technology are various Ti (IV) compounds such as titanium (IV) oxide; titanium (IV) sulfide; titanium (IV) nitrate; titanium (IV) alkoxides such as titanium methoxide, titanium ethoxide, titanium propoxide, titanium isopropoxide, titanium butoxide, titanium 2-ethylhexoxide; and other titanium compounds or complexes including but not limited to titanium phenates; titanium carboxylates such as titanium (IV) 2-ethyl-1-3-hexanedioate or titanium citrate or titanium oleate; and titanium (IV) (triethanolamino)isopropoxide. Other forms of titanium encompassed within the disclosed technology include titanium phosphates such as titanium dithiophosphates (e.g., dialkyldithiophosphates) and titanium sulfonates (e.g., alkylbenzenesulfonates), or, generally, the reaction product of titanium compounds with various acid materials to form salts, such as oil-soluble salts. Titanium compounds can thus be derived from, among others, organic acids, alcohols, and glycols. Ti compounds may also exist in dimeric or oligomeric form, containing Ti—O—Ti structures. Such titanium materials are commercially available or can be readily prepared by appropriate synthesis techniques which will be apparent to the person skilled in the art. They may exist at room temperature as a solid or a liquid, depending on the particular compound. They may also be provided in a solution form in an appropriate inert solvent.

In one embodiment, the titanium can be supplied as a Ti-modified dispersant, such as a succinimide dispersant. Such materials may be prepared by forming a titanium mixed anhydride between a titanium alkoxide and a hydrocarbyl-substituted succinic anhydride, such as an alkenyl- (or alkyl) succinic anhydride. The resulting titanate-succinate intermediate may be used directly or it may be reacted with any of a number of materials, such as (a) a polyamine-based succinimide/amide dispersant having free, condensable —NH functionality; (b) the components of a polyamine-based succinimide/amide dispersant, i.e., an alkenyl- (or alkyl-) succinic anhydride and a polyamine, (c) a hydroxy-containing polyester dispersant prepared by the reaction of a substituted succinic anhydride with a polyol, aminoalcohol, polyamine, or mixtures thereof. Alternatively, the titanate-succinate intermediate may be reacted with other agents such as alcohols, aminoalcohols, ether alcohols, polyether alcohols or polyols, or fatty acids, and the product thereof either used directly to impart Ti to a lubricant, or else further reacted with the succinic dispersants as described above. As an example, 1 part (by mole) of tetraisopropyl titanate may be reacted with about 2 parts (by mole) of a polyisobutene-substituted succinic anhydride at 140-150° C. for 5 to 6 hours to provide a titanium modified dispersant or intermediate. The resulting material (30 g) may be further reacted with a succinimide dispersant from polyisobutene-substituted succinic anhydride and a polyethylenepolyamine mixture (127 grams+diluent oil) at 150° C. for 1.5 hours, to produce a titanium-modified succinimide dispersant.

Another titanium-containing compound may be a reaction product of titanium alkoxide and C6 to C25 carboxylic acid. The reaction product may be represented by the following formula:

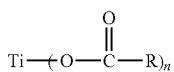

wherein n is an integer selected from 2, 3 and 4, and R is a hydrocarbyl group containing from about 5 to about 24 carbon atoms, or by the formula:

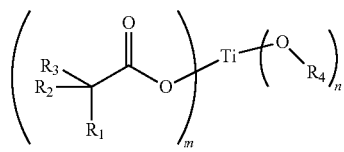

wherein m+n=4 and n ranges from 1 to 3, $R_4$ is an alkyl moiety with carbon atoms ranging from 1-8, $R_1$ is selected from a hydrocarbyl group containing from about 6 to 25 carbon atoms, and $R_2$ and $R_3$ are the same or different and are selected from a hydrocarbyl group containing from about 1 to 6 carbon atoms, or the titanium compound may be represented by the formula:

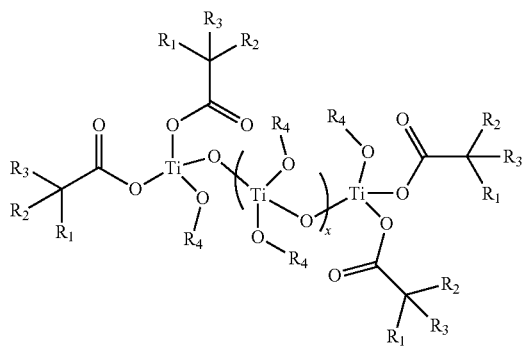

wherein x ranges from 0 to 3, $R_1$ is selected from a hydrocarbyl group containing from about 6 to 25 carbon atoms, $R_2$, and $R_3$ are the same or different and are selected from a hydrocarbyl group containing from about 1 to 6 carbon atoms, and $R_4$ is selected from a group consisting of either H, or $C_6$ to $C_{25}$ carboxylic acid moiety.

Suitable carboxylic acids may include, but are not limited to caproic acid, caprylic acid, lauric acid, myristic acid, palmitic acid, stearic acid, arachidic acid, oleic acid, erucic acid, linoleic acid, linolenic acid, cyclohexanecarboxylic acid, phenylacetic acid, benzoic acid, neodecanoic acid, and the like.

In an embodiment the oil soluble titanium compound may be present in the lubricating oil composition in an amount to provide from 0 to 3000 ppm titanium by weight or 25 to about 1500 ppm titanium by weight or about 35 ppm to 500 ppm titanium by weight or about 50 ppm to about 300 ppm.

Viscosity Index Improvers: The lubricating oil compositions herein also may optionally contain one or more viscosity index improvers. Suitable viscosity index improvers may include polyolefins, olefin copolymers, ethylene/propylene copolymers, polyisobutenes, hydrogenated styrene-isoprene polymers, styrene/maleic ester copolymers, hydrogenated styrene/butadiene copolymers, hydrogenated isoprene polymers, alpha-olefin maleic anhydride copolymers, polymethacrylates, polyacrylates, polyalkyl styrenes, hydrogenated alkenyl aryl conjugated diene copolymers, or mixtures thereof. Viscosity index improvers may include star polymers and suitable examples are described in US Publication No. 20120101017A1.

The lubricating oil compositions herein also may optionally contain one or more dispersant viscosity index improvers in addition to a viscosity index improver or in lieu of a viscosity index improver. Suitable viscosity index improvers may include functionalized polyolefins, for example, ethylene-propylene copolymers that have been functionalized with the reaction product of an acylating agent (such as maleic anhydride) and an amine; polymethacrylates functionalized with an amine, or esterified maleic anhydride-styrene copolymers reacted with an amine.

The total amount of viscosity index improver and/or dispersant viscosity index improver may be about 0 wt. % to about 20 wt. %, about 0.1 wt. % to about 15 wt. %, about 0.1 wt. % to about 12 wt. %, or about 0.5 wt. % to about 10 wt. %, of the lubricating oil composition.

Other Optional Additives: Other additives may be selected to perform one or more functions required of a lubricating fluid. Further, one or more of the mentioned additives may be multi-functional and provide functions in addition to or other than the function prescribed herein.

A lubricating oil composition according to the present disclosure may optionally comprise other performance additives. The other performance additives may be in addition to specified additives of the present disclosure and/or may comprise one or more of metal deactivators, viscosity index improvers, detergents, ashless TBN boosters, friction modifiers, antiwear agents, corrosion inhibitors, rust inhibitors, dispersants, dispersant viscosity index improvers, extreme pressure agents, antioxidants, foam inhibitors, demulsifiers, emulsifiers, pour point depressants, seal swelling agents and mixtures thereof. Typically, fully-formulated lubricating oil will contain one or more of these performance additives.

Suitable metal deactivators may include derivatives of benzotriazoles (typically tolyltriazole), dimercaptothiadiazole derivatives, 1,2,4-triazoles, benzimidazoles, 2-alkyldithiobenzimidazoles, or 2-alkyldithiobenzothiazoles; foam inhibitors including copolymers of ethyl acrylate and 2-ethylhexylacrylate and optionally vinyl acetate; demulsifiers including trialkyl phosphates, polyethylene glycols, polyethylene oxides, polypropylene oxides and (ethylene oxide-propylene oxide) polymers; pour point depressants including esters of maleic anhydride-styrene, polymethacrylates, polyacrylates or polyacrylamides.

Suitable foam inhibitors include silicon-based compounds, such as siloxane.

Suitable pour point depressants may include a polymethylmethacrylates or mixtures thereof. Pour point depressants may be present in an amount sufficient to provide from about 0 wt. % to about 1 wt. %, about 0.01 wt. % to about 0.5 wt. %, or about 0.02 wt. % to about 0.04 wt. % based upon the final weight of the lubricating oil composition.

Suitable rust inhibitors may be a single compound or a mixture of compounds having the property of inhibiting corrosion of ferrous metal surfaces. Non-limiting examples of rust inhibitors useful herein include oil-soluble high molecular weight organic acids, such as 2-ethylhexanoic acid, lauric acid, myristic acid, palmitic acid, oleic acid, linoleic acid, linolenic acid, behenic acid, and cerotic acid, as well as oil-soluble polycarboxylic acids including dimer and trimer acids, such as those produced from tall oil fatty acids, oleic acid, and linoleic acid. Other suitable corrosion inhibitors include long-chain alpha, omega-dicarboxylic acids in the molecular weight range of about 600 to about 3000 and alkenylsuccinic acids in which the alkenyl group contains about 10 or more carbon atoms such as, tetrapropenylsuccinic acid, tetradecenylsuccinic acid, and hexadecenylsuccinic acid. Another useful type of acidic corrosion inhibitors are the half esters of alkenyl succinic acids having about 8 to about 24 carbon atoms in the alkenyl group with alcohols such as the polyglycols. The corresponding half amides of such alkenyl succinic acids are also useful. A useful rust inhibitor is a high molecular weight organic acid.

The rust inhibitor, if present, can be used in an amount sufficient to provide about 0 wt. % to about 5 wt. %, about 0.01 wt. % to about 3 wt. %, about 0.1 wt. % to about 2 wt. %, based upon the final weight of the lubricating oil composition.

In general terms, a suitable lubricant including the neutral to overbased and sulfurized alkyl phenate product herein may include additive components in the ranges listed in the following table.

TABLE 2

Suitable Lubricating Compositions

| Component | Wt. % (Suitable Embodiments) | Wt. % (Suitable Embodiments) |
|---|---|---|
| Neutral/Overbased and sulfurized alkyl phenate | 0.02-5.0 | 0.2-2.0 |
| Succinimide Dispersant(s) | 0-8.0 | 1-6.0 |
| Antioxidant(s) | 0.1-5.0 | 0.01-3.0 |
| Detergent(s) | 0.0-15.0 | 0.2-8.0 |
| Ashless TBN booster(s) | 0.0-1.0 | 0.01-0.5 |
| Corrosion inhibitor(s) | 0.0-5.0 | 0.0-2.0 |
| Metal dihydrocarbyldithiophosphate(s) | 0.0-6.0 | 0.1-4.0 |
| Ash-free phosphorus compound(s) | 0.0-6.0 | 0.0-4.0 |
| Antifoaming agent(s) | 0.0-5.0 | 0.001-0.15 |
| Antiwear agent(s) | 0.0-1.0 | 0.0-0.8 |
| Pour point depressant(s) | 0.0-5.0 | 0.01-1.5 |
| Viscosity index improver(s) | 0.0-25.0 | 0.1-15.0 |
| Dispersant viscosity index improver(s) | 0.0-10.0 | 0.0-5.0 |
| Friction modifier(s) | 0.00-5.0 | 0.01-2.0 |
| Base oil | Balance | Balance |
| Total | 100 | 100 |

The percentages of each component above represent the weight percent of each component, based upon the weight of the final lubricating oil composition. The remainder of the lubricating oil composition consists of one or more base oils. Additives used in formulating the compositions described herein may be blended into the base oil individually or in various sub-combinations. However, it may be suitable to blend all of the components concurrently using an additive concentrate (i.e., additives plus a diluent, such as a hydrocarbon solvent). Fully formulated lubricants conventionally contain an additive package, referred to herein as a dispersant/inhibitor package or DI package, that will supply the characteristics that are required in the formulation.

EXAMPLES

The following examples are illustrative of exemplary embodiments of the disclosure. In these examples, as well as elsewhere in this application, all ratios, parts, and percentages are by weight unless otherwise indicated. It is intended that these examples are being presented for the purpose of illustration only and are not intended to limit the scope of the invention disclosed herein.

For samples with un-sulfurized alkyl phenol/phenate levels of about 0.3 weight percent or greater, the concentration of un-sulfurized alkyl phenol/phenate was determined, for instance, by reverse phase High Performance Liquid Chromatography (HPLC). In an exemplary HPLC method, samples were prepared by weighing about 80 to 120 mg into a 10 ml volumetric flask, diluting to the level mark with methylene chloride, and mixing until the sample is fully dissolved. The HPLC system used in the HPLC method included a HPLC pump, a thermostatted HPLC column compartment, HPLC fluorescence detector, and PC-based chromatography data acquisition system. An exemplary system is an Agilent 1200 HPLC with ChemStation software or equivalent. The HPLC column was a Phenomenex Luna C8(2) 150×4.6 mm 5 μm 100 Å or equivalent. The following system settings were used in performing an analyses: Pump flow=1.0 ml/min, Maximum pressure=200 bars, Fluorescence wavelength: 225 excitation 313 emission: Gain=9, Column Thermostat temperature=25 C, Injection Size=1 μL of diluted sample, Elution type: Gradient, reverse phase, Gradient: 0-7 min 85/15 methanol/water switching to 100% methanol linear gradient, and Run time: 17 minutes For inventive samples having low or ultra-low levels of un-sulfurized alkyl phenate/phenol (such as those below 0.2 weight percent), the methods above are not generally sensitive enough to measure such low levels of un-sulfurized alkyl phenate/alkyl phenol. Rather, the measurement was performed consistent to the above method but modified using a sample having a target phenate concentration of 5 mg/ml and as follows using liquid chromatography-mass spectrometry (LC-MS) using single quad or triple quad MS or equivalent via an Agilent MS 6420 QQQ equipped with and Agilent MSD XT equipped with Agilent 1260 LC Column, such as a Supelco Ascentis Express RP Amide 2.7u, 100 mm×2.1 mmID column or equivalent equipment. For inventive sample measurement, the following system settings were used in the analysis: column temperature 45 C, flow rate of 0.3 ml/min, injection volume of 3 μl, and run time of 22 minutes. The MS system setting and conditions are as follows: ion source: ESI negative, mode SIM, gas temp of 300 C, gas flow 13 l/min, nebulizer 35 psi, capillary 3000 (v), fragmentor of 135, and peak width of 0.07. The percentage of un-sulfurized alkyl phenol/alkyl phenate was determined using a MassHunter Quant Program or equivalent to generate a calibration curve and then to calculate the percent of un-sulfurized alkyl phenol/phenate in the sample.

Example 1

A commercially available calcium phenate (Afton Chemical) having a TBN of 250 and a residual level of un-sulfurized tetrapropylene phenol (TPP) of about 1.5 weight percent was post-treated with methyl triazine using the following procedure: 500 grams of the calcium phenate (starting TPP 1.5%) was charged into a 2-liter reactor, the temperature was then raised to about 120° C. About 125 grams of methyl triazine was then added, and the mixture was reacted at about 150° C. for about 4 hours. Analytical results did not detect the presence of any residual or un-sulfurized TPP.

Example 2

A calcium phenate product was first prepared as follows: about 509 grams of tetrapropylene phenol (TPP), about 336 gram of a slurry made from $Ca(OH)_2$ and base oil, about 60 gram of ethylene glycol, and about 85 grams of recycled base oil were charged to a 2-liter reactor. The reactor temperature was then raised to about 135° C. and held for about 4 hours. Then, about 125 grams of elemental sulfur was charged into reactor, the temperature raised to about 230° C., and held for about 7 hours. After the 7-hour cooking, the reaction was cooled to about 165° C. and then about 27 grams of a neutral calcium sulfonate was added (TBN of 150 and providing about 2.6 weight percent calcium) and about 438 grams of slurry made from $Ca(OH)_2$ and base oil. Lastly, the composition was overbased by introducing carbon dioxide at a rate of about 0.5 liter/minutes for about 5 hours and 30 minutes. The resultant product has a residual or un-sulfurized TPP content of about 1.5%.

About half of the above calcium phenate product was then charged into a 2-liter reactor, heated to about 150° C., and then about 20 grams of methyl triazine was added. The mixture was then reacted for about 2 hours at about 150° C. with a nitrogen sweep. Thereafter, the temperature was increased to about 200° C. and held under max vacuum and nitrogen for about 1 to 2 hours, cooled to about 200° C., and filtered by vacuum and with a celite Hyflo supercell. The resultant product has a residual or un-sulfurized TPP content of about 0.23%.

It is noted that, as used in this specification and the appended claims, the singular forms "a," "an," and "the," include plural referents unless expressly and unequivocally limited to one referent. Thus, for example, reference to "an antioxidant" includes two or more different antioxidants. As used herein, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

It is to be understood that each component, compound, substituent or parameter disclosed herein is to be interpreted as being disclosed for use alone or in combination with one or more of each and every other component, compound, substituent or parameter disclosed herein.

It is further understood that each range disclosed herein is to be interpreted as a disclosure of each specific value within the disclosed range that has the same number of significant digits. Thus, for example, a range from 1 to 4 is to be interpreted as an express disclosure of the values 1, 2, 3 and 4 as well as any range of such values.

It is further understood that each lower limit of each range disclosed herein is to be interpreted as disclosed in combination with each upper limit of each range and each specific value within each range disclosed herein for the same component, compounds, substituent or parameter. Thus, this disclosure to be interpreted as a disclosure of all ranges derived by combining each lower limit of each range with each upper limit of each range or with each specific value within each range, or by combining each upper limit of each range with each specific value within each range. That is, it is also further understood that any range between the endpoint values within the broad range is also discussed herein. Thus, a range from 1 to 4 also means a range from 1 to 3, 1 to 2, 2 to 4, 2 to 3, and so forth.

Furthermore, specific amounts/values of a component, compound, substituent or parameter disclosed in the description or an example is to be interpreted as a disclosure of either a lower or an upper limit of a range and thus can be combined with any other lower or upper limit of a range or specific amount/value for the same component, compound, substituent or parameter disclosed elsewhere in the application to form a range for that component, compound, substituent or parameter.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A sulfurized metal phenate detergent comprising a compound of Formula I and a compound of Formula II:

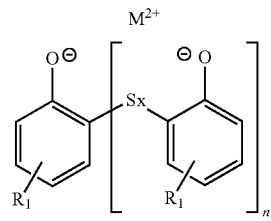

(Formula I)

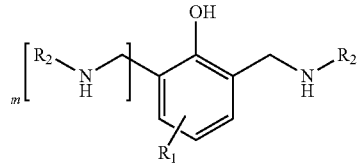

(Formula II)

wherein
- each $R_1$, independently, is a C12 to C20 alkyl group;
- $R_2$ is hydrogen, an alkyl group, an alkylamino group, or a hydroxyalkyl group;
- x is an integer from 1 to 4;
- n is an integer from 1 to 3;
- m is an integer of 0 or 1; and
- $M^{2+}$ is a divalent metal ion.

2. The sulfurized metal phenate detergent of claim 1, wherein $R_2$ is methyl.

3. The sulfurized metal phenate detergent of claim 1, wherein $R_2$ has a structure of —$R_4N(R_5)(R_5)$ wherein $R_4$ is a C1 to C10 hydrocarbyl group and each $R_5$ is, independently, a C1 to C4 alkyl group.

4. The sulfurized metal phenate detergent of claim 1, wherein the detergent includes about 0.01 to about 0.5 weight percent of the compound of Formula II.

5. The sulfurized metal phenate detergent of claim 4, further comprising about 0.5 weight percent or less of an unsulfurized alkyl phenol.

6. The sulfurized metal phenate detergent of claim 1, wherein the detergent has a TBN of 0 to 300 mg KOH as measured by the method of ASTM D-2896.

7. The sulfurized metal phenate detergent of claim 1, wherein each of the compound of Formula I, the compound of Formula II, or both has less than about 15 weight percent of $R_1$ substitution at the ortho position.

8. The sulfurized metal phenate detergent of claim 1, wherein the detergent includes up to about 100,000 ppm of the metal provided by an alkali or alkaline metal and up to about 65,000 ppm of sulfur.

9. The sulfurized metal phenate detergent of claim 8, wherein the alkali or alkaline metal is one of lithium, potassium, sodium, magnesium, calcium, barium, aluminum, or combinations thereof.

10. A sulfurized metal phenate detergent comprising a compound of Formula I and a compound of Formula II:

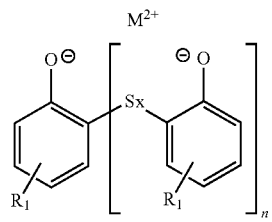
(Formula I)

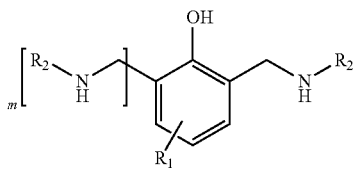
(Formula II)

wherein
- each $R_1$, independently, is an alkyl group, an aryl group, an alkylaryl group, or arylalkyl group;
- $R_2$ is hydrogen, an alkyl group, an alkylamino group, or a hydroxyalkyl group;
- x is an integer from 1 to 4;
- n is an integer from 1 to 3;
- m is an integer of 0 or 1; and
- $M^{2+}$ is a divalent metal ion, and wherein the detergent includes about 0.01 to about 0.5 weight percent of the compound of Formula II.

11. The sulfurized metal phenate detergent of claim 10, wherein $R_1$ is a C8 to C20 alkyl group.

12. The sulfurized metal phenate detergent of claim 10, wherein $R_2$ is methyl.

13. The sulfurized metal phenate detergent of claim 10, wherein $R_2$ has a structure of —$R_4N(R_5)(R_5)$ wherein $R_4$ is a C1 to C10 hydrocarbyl group and each $R_5$ is, independently, a C1 to C4 alkyl group.

14. The sulfurized metal phenate detergent of claim 10, wherein the detergent has a TBN of 0 to 300 mg KOH as measured by the method of ASTM D-2896.

15. The sulfurized metal phenate detergent of claim 10, wherein each of the compound of Formula I, the compound of Formula II, or both has less than about 15 weight percent of $R_1$ substitution at the ortho position.

16. A sulfurized metal phenate detergent comprising a compound of Formula I and a compound of Formula II:

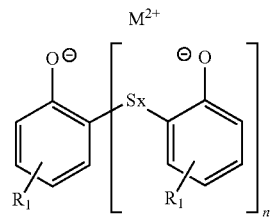
(Formula I)

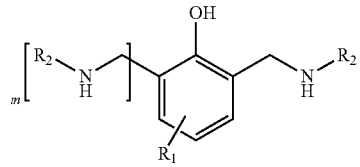
(Formula II)

wherein
- each $R_1$, independently, is an alkyl group, an aryl group, an alkylaryl group, or arylalkyl group;
- $R_2$ is hydrogen, an alkyl group, an alkylamino group, or a hydroxyalkyl group;
- x is an integer from 1 to 4;
- n is an integer from 1 to 3;
- m is an integer of 0 or 1; and
- $M^{2+}$ is a divalent metal ion, and
- wherein the detergent includes up to about 100,000 ppm of the metal provided by an alkali or alkaline metal and up to about 65,000 ppm of sulfur.

17. The sulfurized metal phenate detergent of claim 16, wherein $R_1$ is a C8 to C20 alkyl group.

18. The sulfurized metal phenate detergent of claim 16, wherein $R_2$ is methyl.

19. The sulfurized metal phenate detergent of claim 16, wherein $R_2$ has a structure of —$R_4N(R_5)(R_5)$ wherein $R_4$ is a C1 to C10 hydrocarbyl group and each $R_5$ is, independently, a C1 to C4 alkyl group.

20. The sulfurized metal phenate detergent of claim 16, wherein each of the compound of Formula I, the compound of Formula II, or both has less than about 15 weight percent of $R_1$ substitution at the ortho position.

* * * * *